(12) United States Patent
Soriano et al.

(10) Patent No.: US 6,461,864 B1
(45) Date of Patent: Oct. 8, 2002

(54) METHODS AND VECTOR CONSTRUCTS FOR MAKING NON-HUMAN ANIMALS WHICH UBIQUITOUSLY EXPRESS A HETEROLOGOUS GENE

(75) Inventors: Philippe Soriano, Seattle, WA (US); Elizabeth J. Robertson, Cambridge, MA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 09/291,541

(22) Filed: Apr. 14, 1999

Related U.S. Application Data

(60) Provisional application No. 60/081,894, filed on Apr. 15, 1998.

(51) Int. Cl.[7] ............................ C12N 15/63; C12N 15/87
(52) U.S. Cl. ..................... 435/320.1; 435/463; 435/462
(58) Field of Search .................................. 435/455, 462, 435/463, 440

(56) References Cited

U.S. PATENT DOCUMENTS

| | | | |
|---|---|---|---|
| 4,683,202 A | | 7/1987 | Mullis .......................... 435/91 |
| 5,464,764 A | * | 11/1995 | Capecchi et al. ......... 435/172.3 |
| 5,627,059 A | | 5/1997 | Capecchi et al. ........... 435/455 |
| 5,631,153 A | | 5/1997 | Capecchi et al. ........... 435/455 |

OTHER PUBLICATIONS

F Parker et al., Molecular and Cellular Biology, "A Ras–GTPase–Activating Protein SH3–Domain–Binding Protein," Jun. 1996, vol. 16, No. 6, pp. 2561–2569.*

Ludwig DL et al. Transgenic Research 5:385–395, 1996.*
Skarnes WC. Current Opinion in Biotechnology 4:684–689, 1993.*
Yagi T et al. Anal Biochem 214:77–86, 1993 (abstract).*
Kilby NJ Trends in Genetics 9:413–421, 1993.*
Wang et al., "Targeted DNA recombination in vivo using an adenovirus carrying the cre recombinase gene," *Proc. Natl. Acad. Sci. USA* 93:3932–3936 (Apr., 1996).

(List continued on next page.)

*Primary Examiner*—Dave T. Nguyen
*Assistant Examiner*—Ram R. Shukla
(74) *Attorney, Agent, or Firm*—Townsend and Townsend and Crew LLP

(57) ABSTRACT

Transgenic non-human animals one having a general deletor construct and a second having a general reporter construct are described. The general deletor animals express a heterologous recombinase under the control of an ubiquitously expressed endogenous promoter. Specifically, the Cre recombinase is inserted into the ROSA26 locus of the mouse. The general reporter animals have a gene which is desired to remove flanked by sites recognized by the is heterologous recombinase. This flanked sequence is operatively associated with a marker gene such that when the gene sequence flanked by sites recognized by the heterologous recombinase is excised, the reporter gene is expressed. When the general deletor mouse is crossed with the general reporter mouse the heterologous recombinase is expressed in essentially all cells of the resultant descendants under the control of the ubiquitous promoter. Expression of the recombinase results in the excision of the desired gene in essentially all cells of the descendant animals. A conditional deletor construct and its use to derive a conditional deletor animal are also described.

48 Claims, 4 Drawing Sheets

OTHER PUBLICATIONS

Kolb et al., "Genomic targeting of a bicistronic DNA fragment by Cre-mediated site-specific recombination," *Gene* 203:209–216 (1997).

Tocque et al., "Ras–GTPase Activating Protein (GAP): A Putative Effector for Ras," *Cell. Signal.* (9)2:153–158 (1997).

Meyers et al., "An Fgf8 mutant allelic series generated by Cre- and Flp-mediated recombination," *Nature Genetics* 18:136–141 (Feb., 1998).

Drago et al., "Targeted Expression of a Toxin Gene to D1 Dopamine Receptor Neurons by Cre-Mediated Site-Specific Recombination," *J. Neuroscience* 18:9845–9857 (Dec. 1, 1998).

Vidal et al., "Cre Expression in Primary Spermatocytes: A Tool for Genetic Engineering of the Germ Line," *Mol. Reprod. Dev.* 51:274–280 (1998).

Shawlot et al., "Restricted beta–glactosidase expression of a hygromycin lacZ gene targeted to the beta–actin locus and embryonic lethality of beta–actin mutant mice," *Transgenic Res.* 7:95–103 (1998).

Doetschman et al., "The in vitro development of blastocyst–derived embryonic stem cell lines: formation of visceral yolk sac, blood islands and myocardium," *J. Embryol. Exp. Morph.* 87:27–45 (1985).

Robertson et al., "Germ–line transmission of genes introduced into cultured pluripotential cells by retroviral vector," *Nature* 323:445–448 (1986).

Vijaya et al., "Acceptor Sites for Retroviral Integrations Map Near DNase I–Hypersensitive Sites in Chromatin," *J. Virol.* 60:683–692 (1986).

Hooper et al., "HPRT–deficient (Lesch–Nyhan) mouse embryos derived from germline colonization by cultured cells," *Nature* 326:292–295 (1987).

Rohdewohld et al., "Retrovirus Integration and Chromatin Structure: Moloney Murine Leukemia Proviral Integration Sites Map Near Dnase I–Hypersensitive Sites," *J. Virol.* 61:336–343 (1987).

Kogan et al., "An Improved Method for Prenatal Diagnosis of Genetic Diseases by Analysis of Amplified DNA Sequences," *New England J. Med.* 317:985–990 (1987).

Sauer and Henderson, "Site–specific DNA recombination in mammalian cells by the Cre recombinase of bacteriophage P1," *Proc. Natl. Acad. Sci. USA* 85:5166–5170 (1988).

Jang et al., "A Segment of the 5' Nontranslated Region of Encephalomyocarditis Virus RNA Directs Internal Entry of Ribosomes during In Vitro Translation," *J. Virol.* 62:2636–2643 (1988).

Jang et al., "Initiation of Protein Synthesis by Internal Entry of Ribosomes into the 5' Nontranslated Region of Encephalomyocarditis Virus RNA In Vivo," *J. Virol.* 63:1651–1660 (1989).

Joyner et al., "Production of a mutation in mouse En–2 gene by homologous recombination in embryonic stem cells," *Nature* 338:153–156 (1989).

Beddington and Robertson, "An assessment of the developmental potential of embryonic stem cells in the midgestation mouse embryo," *Development* 105:733–737 (1989).

Zjilstra et al., "Germ–line Transmission of a disrupted $\beta_2$—microglobulin gene produced by homologous recombination in embryonic stem cells," *Nature* 342:435–438 (1989).

Schwartzberg et al., "Germ–Line Transmission of a c–abl Mutation Produced by Targeted Gene Disruption in ES Cells," *Science* 246:799–803 (1989).

Shulman et al., "Homologous Recombination in Hybridoma Cells: Dependence on Time and Fragment Length," *Mol. Cell. Biol.* 10:4466–4472 (1990).

McMahon and Bradley, "The Wnt–1 (int–1) Proto–Oncogene is Required for Development of a Large Region of the Mouse Brain," *Cell* 62:1073–1085 (1990).

Jang and Wimmer, "Cap–independent translation of encephalomyocarditis virus RNA: structural elements of the internal ribosomal entry site and involvement of a cellular 57–kD RNA–binding protein," *Genes Dev.* 4:1560–1572 (1990).

O'Gorman et al., "Recombinase–Mediated Gene Activation and Site–Specific Integration in Mammalian Cells," *Science* 251:1351–1355 (1991).

Ghattas et al., "The Encephalomyocarditis Virus Internal Ribosome Entry Site Allows Efficient Coexpression of Two Genes from a Recombinant Provirus in Cultured Cells and in Embryos," *Mol. Cell. Biol.* 11:5848–5859 (1991).

Mortensen, et al., "Embryonic stem cells lacking a functional inhibitory G–protein subunit ($\alpha_{i2}$) produced by gene targeting of both alleles," *Proc. Natl. Acad. Sci. USA* 88:7036–7040 (1991).

Soriano et al., "Targeted Disruption of the c–src Proto–Oncogene Leads to Osteopetrosis in Mice," *Cell* 64: 693–702 (1991).

Lumsden et al., "Segmental origin and migration or neural crest cells in the hindbrain region of the chick embryo," *Development* 113:1281–1291 (1991).

Friedrich and Soriano, "Promoter traps in embryonic stem cells: a genetic screen to identify and mutate developmental genes in mice," *Genes Dev.* 5:1513–1523 (1991).

Hasty et al. "The Length of Homology Required for Gene Targeting in Embryonic Stem Cells," *Mol. Cell. Biol.* 11:5586–5591 (1991).

Mattila et al., "Fidelity of DNA synthesis by the *Thermococcus litoralis* DNA polymerase—an extremely heat stable enzyme with proofreading activity," *Nucl. Acids Res.* 19:4967–4973 (1991).

Valancius and Smithies, "Testing an "In–Out" Targeting Procedure for Making Subtle Genomic Modifications in Mouse Embryonic Stem Cells," *Mol. Cell. Biol.* 11:1402–1408 (1991).

Donehower et al., "Mice deficient for p53 are developmentally normal but susceptible to spontaneous tumours," *Nature* 356:215–221 (1992).

Pilipenko et al., "Prokaryotic–like Cis Elements in the Cap–Independent Internal Initiation of Translation on Picornavirus RNA," *Cell* 68:119–131 (1992).

Berinstein et al., "Gene Replacement with One–Sided Homologous Recombination," *Mol. Cell. Biol.* 12:360–367 (1992).

Gu et al., "Independent Control of Immunoglobulin Switch Recombination at Individual Switch Regions Evidenced through Cre–loxP–Mediated Gene Targeting," *Cell* 73:1155–1164 (1993).

Mountford et al., "Dicistronic targeting constructs: Reporters and modifiers of mammalian gene expression," *Proc. Natl. Acad. Sci. USA* 91:4303–4307 (1994).

Ganju et al., "The Eck receptor tyrosine kinase is implicated in pattern formation during gastrulation, hindbrain segmentation and limb development," *Oncogene* 9:1613–1624 (1994).

Ruiz and Robertson, "The expression of the receptor–protein tyrosine kinase gene, eck, is highly restricted during early mouse development," *Mech. Dev.* 46:87–100 (1994).

Zhuang et al., "The Helix–Loop–Helix Gene E2A is Required for B Cell Formation," *Cell* 79:875–884 (1994).

Chen and Behringer, "twist is required in head mesenchyme for cranial neural tube morphogenesis," *Gen. Dev.* 9:686–699 (1995).

Kennedy et al, "Identification of a Mouse Orthologue of the Human ras–GAP–SH3–Domain Binding Protein and Structural Confirmation that these Proteins Contain an RNA Recognition Motif," *Biomed. Pept. Prot. Nucl. Acids* 2:93–99 (1997).

Collignon et al., "Relationship between asymmetric nodal expression and the direction of embryonic turning," *Nature* 381:155–158 (1996).

Chen et al., "Germ–line inactivation of the murine Eck receptor tyrosine kinase by gene trap retroviral insertion," *Oncogene* 12:979–988 (1996).

Gale et al., "Eph Receptors and Ligands Comprise Two Major Specificity Subclasses and are Reciprocally Compartmentalized during Embryogenesis," *Neuron* 17:9–19 (1996).

Kontges and Lumsden, "Rhombencephalic neural crest segmentation is preserved throughout craniofacial ontogeny," *Development* 122:3229–3242 (1996).

Zambrowicz et al., "Disruption of overlapping transcripts in the ROSA βgeo 26 gene trap strain leads to widespread expression of β–galactosidase in mouse embryos and hematopoietic cells," *Proc. Natl. Acad. Sci. USA* 94:3789–3794 (1997).

Soriano, "The PDGFα receptor is required for neural crest cell development and for normal patterning of the somites," *Development* 124: 2691–2700 (1997).

Gallouzi et al., "A Novel Phosphorylation–Dependent RNase Activity of GAP–SH3 Binding Protein: a Potential Link Between Signal Transduction and RNA Stability," *Mol. Cell. Biol.* 18:3956–3965 (1998).

* cited by examiner

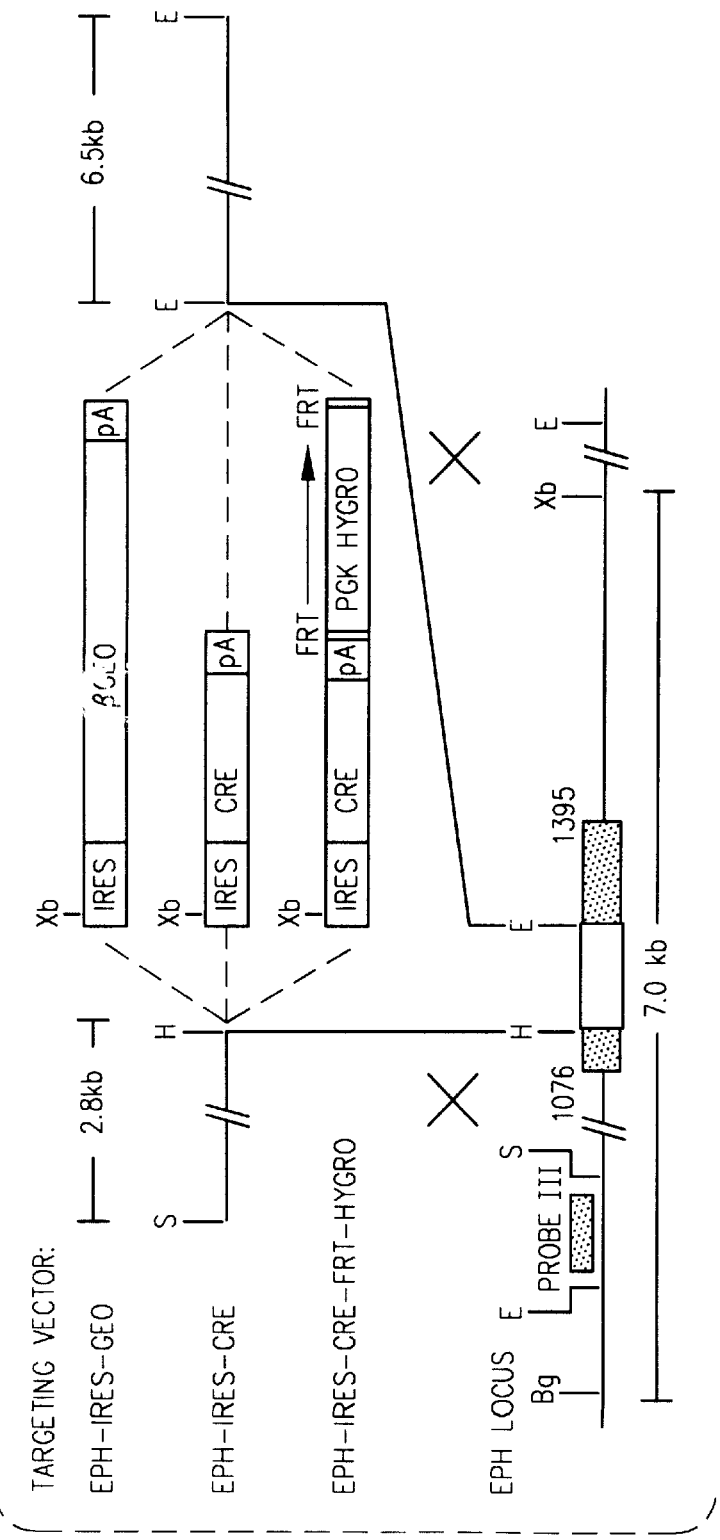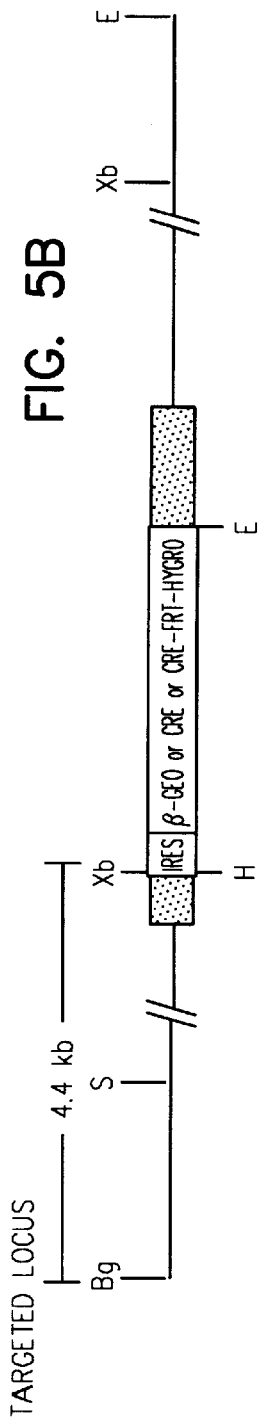

SEQUENCE LISTING

```
<160> NUMBER OF SEQ ID NOS: 28

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PCR primer
      for genotyping

<400> SEQUENCE: 1
ggcttaaagg ctaacctgat gtg                                              23

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: PCR primer
      for genotyping

<400> SEQUENCE: 2
gcgaagagtt tgtcctcaac c                                                21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR primer
      for genotyping

<400> SEQUENCE: 3
ggagcgggag aaatggatat g                                                21

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: ROSA26
      exon/specific primer

<400> SEQUENCE: 4
tgcgtttgcg gggatgg                                                     17

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Splice
      acceptor specific primer

<400> SEQUENCE: 5
gcgaagagtt tgtcctcaac                                                  20
```

<210> SEQ ID NO 6
<211> LENGTH: 534
<212> TYPE: DNA
<213> ORGANISM: Murine DNA sequence of ROSA26 gene locus promoter 1

<400> SEQUENCE: 6

```
ctcgagttag gcccaacgcg gcgccacggc gtttcctggc cgggaatggc ccgtacccgt      60
gaggtggggg tgggggggcag aaaaggcgga gcgagcccga ggcggggagg gggagggcca    120
ggggcggagg gggccggcac tactgtgttg gcggactggg gggactaggg ctgcgtgagt    180
ctctgagcgc aggcgggcgg cggccgcccc tccccggcg gcggcagcgg cggcagcggc    240
ggcagctcac tcagcccgct gcccgagcgg aaacgccact gaccgcacgg ggattcccag    300
tgccggcgcc aggggcacgc gggacacgcc ccctcccgcc gcgccattgg cctctccgcc    360
caccgcccca cacttattgg ccgtgcgcc gccaatcagc ggaggctgcc ggggccgcct    420
aaagaagagg ctgtgctttg gggctccggc tcctcagaga gcctcggcta ggtaggggat    480
cgggactctg gcgggagggc ggcttggtgc gtttgcgggg atgggcggcc gcgg           534
```

<210> SEQ ID NO 7
<211> LENGTH: 1161
<212> TYPE: DNA
<213> ORGANISM: Murine nucleotide sequence of ROSA26 transcript 1

<400> SEQUENCE: 7

```
ggctcctcag agagcctcgg ctaggtaggg gatcgggact ctggcgggag ggcggcttgg      60
tgcgtttgcg gggatgggcg gccgcggcag gccctccgag cgtggtggag ccgttctgtg    120
agacagccgg atcattcctt gaggacagga cagtgcttgt ttaaggctat atttctgctg    180
tctgagcagc aacaggtctt cgagatcaac atgatgttca taatcccaag atgttgccat    240
ttatgttctc agaagcaagc agaggcatga tggtcagtga cagtaatgtc actgtgttaa    300
atgttgctat gcagttttgga ttttttctaat gtagtgtagg tagaacatat gtgttctgta    360
tgaattaaac tcttaagtta caccttgtat aatccatgca atgtgttatg caattaccat    420
tttaagtatt gtagctttct ttgtatgtga ggataaaggt gtttgtcata aaatgttttg    480
aacatttccc caaagttcca aattataaaa ccacaacgtt gaacttatt tatgaacaat    540
ggttgtagtt tcatgctttt aaaatgctta attattcaat taacaccgtt tgtgttataa    600
tatatataaa actgacatgt agaagtgttt gtccagaaca tttcttaaat gtatactgtc    660
tttagagagt ttaatatagc atgtcttttg caacatacta acttttgtgt tggtgcgagc    720
aatattgtgt agtcattttg aaaggagtca tttcaatgag tgtcagattg ttttgaatgt    780
tattgaacat tttaaatgca gacttgttcg tgttttagaa agcaaaactg tcagaagctt    840
tgaactagaa attaaaaagc tgaagtattt cagaagggaa ataagctact tgctgtatta    900
gttgaaggaa agtgtaatag cttagaaaat ttaaaaccat atagttgtca ttgctgaata    960
tctggcagat gaaaagaaat actcagtggt tcttttgagc aatataacag cttgttatat   1020
taaaaatttt ccccacagat ataaactcta atctataact cataaatgtt acaaatggat   1080
gaagcttaca aatgtggctt gacttgtcac tgtgcttgtt ttagttatgt gaaagtttgg   1140
caataaacct atgtcctaaa t                                              1161
```

<210> SEQ ID NO 8
<211> LENGTH: 412
<212> TYPE: DNA

<213> ORGANISM: Murine nucleotide sequence of ROSA26 transcript 2

<400> SEQUENCE: 8

```
ctaggtaggg gatcgggact ctggcgggag ggcggcttgg tgcgtttgcg gggatgggcg     60
gccgcggcag gccctccgag cgtggtggag ccgttctgtg agacagccgg atcattcctt   120
gaggacagga cagtgcttgt ttaaggctat atttctgctg tctgagcagc aacaggtctt   180
cgagatcaac atgatgttca taatcccaag atgttgccat ttatgttctc agaagcaagc   240
agaggcatga tggagggtct cttccttcat cttgatctga aggatgaaca aaggcttgag   300
cagtgcgctt tagaagataa actgcagcat gaaggccccc gatgttcacc cagactacat   360
ggacctttcg ccacacatgt cccattccag ataaggcctg cacacacaa aa            412
```

<210> SEQ ID NO 9
<211> LENGTH: 1974
<212> TYPE: DNA
<213> ORGANISM: Murine nucleotide sequence of ROSA26 antisense region

<400> SEQUENCE: 9

```
tcggcttccg gcggcgtgct cgcggtgcgg agaccggaag ggtctgtgct tgctgccgag     60
actgttggtc cttttagaaa catctccatc atgtcttgtg acactcaaga agctaccaga   120
gagtgcctgg gtatgaacct tgatggcaac aaagagcctg tgtcgctggt agaaagcggc   180
gtcagaagtg agtcggagca tctccaagtc actattggag ccactgtacc cactggcttt   240
gaacaaacgg ctgcggggga agtgagagag aaactgaagt cggcctgcag aatcagcaaa   300
gaccgcggaa agatctattt tgatattgca gtggaaagtc tggctcaggt tcattgtctg   360
agatcagttg ataacttgtt tgtggttgtt caggagttta agattacca gttcaaagat   420
acgaaggaag aagttctaag agactttgaa gaactggctg aaaactccc atggtcagac   480
cctttaaaag tctggcaaat taacaccact ttcaagaaga gaaagcaaa gcgcagaaag   540
gcaaatcaga gtgcaggtaa agagaaggct gactgtggac aaggagacaa agcagatgag   600
aaagatggta agaaaaagca tgccagcagc acttcagatt cacatatctt ggactattat   660
gaaaatccag ccatcaaaga agagatatca accttagtag gtgatgtctt gtcgtcttgc   720
aaagatgaaa ctggtcaaag cttaagagaa gaaactgaac cacaggtaca gaagtttaga   780
gtcacctgca acagagcagg agagaaacat tgctttacct ccaatgaggc tgcgagagat   840
tttgggggtg ctattcaaga gtactttaag tggaaggctg atatgaccaa ctttgatgta   900
gaggttctcc tgaacatcca tgataatgaa gtcattgttg ctattgcact gacagaagag   960
agtctccatc gcagaaatat tacacatttt ggacctacaa ctcttaggtc aactcttgcc  1020
tatgggatgc tcaggctctg tgaacctaag cctactgatg taatagtgga cccaatgtgt  1080
ggaacagggg caataccaat agagggggct actgagtggt ctcactgtta ccatattgct  1140
ggggacaata acccactggc agtgaacaga gcagcaaata acatctcatc tctattgact  1200
aagagccaga ttaaagatgg aaaaacaacc tggggtttgc ccattgatgc tgttcagtgg  1260
gatatctgca acctcccact gagaactgct tctgtggata ttattgtaac agatatgcca  1320
tttgaaaaaa ggatgggatc caagaagaga aattggaatc tctatccagc ttgccttcgg  1380
gaaatgagcc gtgtctgtag accagggaca ggcagagctg tactgcttac tcaggacaag  1440
aaatgtttta ccaaggcctt atctggaatg ggacatgtgt ggcgaaaggt ccatgtagtc  1500
tgggtgaaca tcggggcct tcatgctgca gtttatcttc taaagcgcac tgctcaagcc  1560
tttgttcatc cttcagatca agatgaagga agagaccctc cttggtaaag aaaagagtga  1620
```

-continued

```
agacaactta ttaatatttg tagttcctaa cactggaaat atcagcataa agaacttgct    1680
ttgggagaaa aatagcagaa aagtaactta cagtacaggt tacactgctt gaccactcca    1740
gaatgcttga tttctagcaa ggtgattgta atggtatttc ttaagaagcc tacactgctt    1800
ggcttctaag tgtcagaaca ctttaggcca tattctattg cttgtgcaac ctactgtttt    1860
atggtctaaa ttctttgtat catctcagaa gcagaagtat cccttaagat ctacagtttt    1920
atcatctgct ttaaaataaa tatacaacct aaacagagca aaaaaaaaaa aaaa          1974
```

<210> SEQ ID NO 10
<211> LENGTH: 505
<212> TYPE: PRT
<213> ORGANISM: Murine amino acid sequence of ROSA26 antisense region

<400> SEQUENCE: 10

```
Met Ser Cys Asp Thr Gln Glu Ala Thr Arg Glu Cys Leu Gly Met Asn
 1               5                  10                  15

Leu Asp Gly Asn Lys Glu Pro Val Ser Leu Val Glu Ser Gly Val Arg
             20                  25                  30

Ser Glu Ser Glu His Leu Gln Val Thr Ile Gly Ala Thr Val Pro Thr
         35                  40                  45

Gly Phe Glu Gln Thr Ala Ala Gly Glu Val Arg Glu Lys Leu Lys Ser
     50                  55                  60

Ala Cys Arg Ile Ser Lys Asp Arg Gly Lys Ile Tyr Phe Asp Ile Ala
 65                  70                  75                  80

Val Glu Ser Leu Ala Gln Val His Cys Leu Arg Ser Val Asp Asn Leu
                 85                  90                  95

Phe Val Val Val Gln Glu Phe Lys Asp Tyr Gln Phe Lys Asp Thr Lys
            100                 105                 110

Glu Glu Val Leu Arg Asp Phe Glu Glu Leu Ala Gly Lys Leu Pro Trp
        115                 120                 125

Ser Asp Pro Leu Lys Val Trp Gln Ile Asn Thr Thr Phe Lys Lys Lys
    130                 135                 140

Lys Ala Lys Arg Arg Lys Ala Asn Gln Ser Ala Gly Lys Glu Lys Ala
145                 150                 155                 160

Asp Cys Gly Gln Gly Asp Lys Ala Asp Glu Lys Asp Gly Lys Lys Lys
                165                 170                 175

His Ala Ser Ser Thr Ser Asp Ser His Ile Leu Asp Tyr Tyr Glu Asn
            180                 185                 190

Pro Ala Ile Lys Glu Glu Ile Ser Thr Leu Val Gly Asp Val Leu Ser
        195                 200                 205

Ser Cys Lys Asp Glu Thr Gly Gln Ser Leu Arg Glu Glu Thr Glu Pro
    210                 215                 220

Gln Val Gln Lys Phe Arg Val Thr Cys Asn Arg Ala Gly Glu Lys His
225                 230                 235                 240

Cys Phe Thr Ser Asn Glu Ala Ala Arg Asp Phe Gly Gly Ala Ile Gln
                245                 250                 255

Glu Tyr Phe Lys Trp Lys Ala Asp Met Thr Asn Phe Asp Val Glu Val
            260                 265                 270

Leu Leu Asn Ile His Asp Asn Gly Val Ile Val Ala Ile Ala Leu Thr
        275                 280                 285

Glu Glu Ser Leu His Arg Arg Asn Ile Thr His Phe Gly Pro Thr Thr
    290                 295                 300

Leu Arg Ser Thr Leu Ala Tyr Gly Met Leu Arg Leu Cys Glu Pro Lys
```

-continued

```
                305                 310                 315                 320
Pro Thr Asp Val Ile Val Asp Pro Met Cys Gly Thr Gly Ala Ile Pro
                    325                 330                 335
Ile Glu Gly Ala Thr Glu Trp Ser His Cys Tyr His Ile Ala Gly Asp
                340                 345                 350
Asn Asn Pro Leu Ala Val Asn Arg Ala Ala Asn Asn Ile Ser Ser Leu
            355                 360                 365
Leu Thr Lys Ser Gln Ile Lys Asp Gly Lys Thr Thr Trp Gly Leu Pro
        370                 375                 380
Ile Asp Ala Val Gln Trp Asp Ile Cys Asn Leu Pro Leu Arg Thr Ala
385                 390                 395                 400
Ser Val Asp Ile Ile Val Thr Asp Met Pro Phe Gly Lys Arg Met Gly
                    405                 410                 415
Ser Lys Lys Arg Asn Trp Asn Leu Tyr Pro Ala Cys Leu Arg Glu Met
                420                 425                 430
Ser Arg Val Cys Arg Pro Gly Thr Gly Arg Ala Val Leu Leu Thr Gln
            435                 440                 445
Asp Lys Lys Cys Phe Thr Lys Ala Leu Ser Gly Met Gly His Val Trp
        450                 455                 460
Arg Lys Val His Val Val Trp Val Asn Ile Gly Gly Leu His Ala Ala
465                 470                 475                 480
Val Tyr Leu Leu Lys Arg Thr Ala Gln Ala Phe Val His Pro Ser Asp
                    485                 490                 495
Gln Asp Glu Gly Arg Asp Pro Pro Trp
                    500                 505
```

```
<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:  Primer for
      detecting ROSA26 transcript 1 and 2 (R26GSPQ)

<400> SEQUENCE: 11
gccgttctgt gagacag                                                      17

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer for
      detecting ROSA26 transcript 1 and 2 (Qo)

<400> SEQUENCE: 12
aaatgttctg gacaaacact tc                                                22

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer for
      detecting ROSA26 transcript 2 (R26B)

<400> SEQUENCE: 13
cgcactgctc aagcctttgt t                                                 21

<210> SEQ ID NO 14
```

```
<211> LENGTH: 19
<212> TYPE: DNA
<213> ORGANISM: Artificial Sequence
<220> FEATURE:
<223> OTHER INFORMATION: Description of Artificial Sequence:  Primer for
      detecting ROSA26 antisense region (R26alt2)

<400> SEQUENCE: 14
taactccagt tctaggggg                                                  19

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Primter for
      detecting ROSA26 antisense region (ROSA26i2-F1)

<400> SEQUENCE: 15
ggtcaagcag tgtaacctg                                                  19

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer for
      mutating Kozak ATG to BamHI site (ROSA265'-mutR)

<400> SEQUENCE: 16
cggatccccg caaacgcacc aa                                              22

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:   PCR
      primer from ROSA26 promoter

<400> SEQUENCE: 17
cctaaagaag aggctgtgct ttgg                                            24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: PCR primer
      from ROSA26 splice acceptor

<400> SEQUENCE: 18
catcaaggaa accctggact actg                                            24

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: PCR primer 1

<400> SEQUENCE: 19
taatgggata ggttacg                                                    17

<210> SEQ ID NO 20
<211> LENGTH: 23
<212> TYPE: DNA
```

```
<213> ORGANISM: Artificial Sequence
<220> FEATURE:
<223> OTHER INFORMATION: Description of Artificial Sequence: PCR primer 2

<400> SEQUENCE: 20
ggttgtgagc tcttctagat ggt                                              23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:   PCR adapter
      primer 2

<400> SEQUENCE: 21
ggttgtgagc tcttctagat gg                                               22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: PCR primer
      specific to ROSA(beta)geo vector

<400> SEQUENCE: 22
agtatcggcc tcaggaagat cg                                               22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:   PCR nested
      vector primer

<400> SEQUENCE: 23
attcaggctg cgcaactgtt gg                                               22

<210> SEQ ID NO 24
<211> LENGTH: 52
<212> TYPE: DNA
<213> ORGANISM: Artificial Sequence
<220> FEATURE:
<223> OTHER INFORMATION: Description of Artificial Sequence: loxP
      oligomer with cohesive NcoI and HindIII termini

<400> SEQUENCE: 24
catggccaga tctagaataa cttcgtatag catacattat acgaagttat ca              52

<210> SEQ ID NO 25
<211> LENGTH: 14
<212> TYPE: DNA
<213> ORGANISM: Encephalomyocarditis virus

<400> SEQUENCE: 25
cgatgattat atgg                                                        14

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: PGK NEO
      IRES - CRE #1
```

-continued

```
<400> SEQUENCE: 26
cgatgattat atgccc                                                    16

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:  PGK NEO
      IRES - CRE #2

<400> SEQUENCE: 27
cgatgataag ctctagactc gaccatgccc                                     30

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: PGK NEO
      IRES - CRE #3

<400> SEQUENCE: 28
cgatgataag cttatgccc                                                 19
```

METHODS AND VECTOR CONSTRUCTS FOR MAKING NON-HUMAN ANIMALS WHICH UBIQUITOUSLY EXPRESS A HETEROLOGOUS GENE

CROSS REFERENCE TO RELATED APPLICATIONS

This application claims the benefit of U.S. Provisional Application No. 60/081,894, filed Apr. 15, 1998.

GOVERNMENT SUPPORT

The U.S. government may have certain rights in the invention pursuant to Grant No. HD 24875 received from the U.S. National Institutes of Health.

BACKGROUND OF THE INVENTION

Gene traps provide a general strategy to identify genes exhibiting discrete patterns of expression during development and differentiation. The basic design of gene trap vectors has been based on the introduction of a promoterless reporter gene, e.g., β-galactosidase, into embryonic stem (ES) cells, which could only be expressed if the reporter gene has integrated in the right frame and orientation within a transcriptional unit. To improve the chances of expression, the reporter gene has been placed. downstream of a splice acceptor (SA) sequence allowing expression to occur when the reporter gene is integrated within an intron. Integration results in reporter gene expression that reflects the expression pattern of the endogenous gene or is influenced by nearby transcriptional regulatory elements.

One method of constructing trap vectors has been to use as a background a retroviral vector. Retroviruses integrate into the genome with no rearrangements of flanking sequences. This is not always the case when DNA is introduced by microinjection and perhaps other methods. An additional advantage of using a retroviral vector has been that the sites of proviral integration are often found close to hypersensitive sites (Vijaya et al., *J. Virol.* 60:683–692 (1986); Rohdewohld et al., *J. Virol.* 61:336–343 (1987)).

In one particular design the reporter gene is inserted in Reverse Orientation (with respect to retroviral transcription) downstream of a Slice Acceptor sequence, and the resultant mice are referred to as ROSA. Using this gene trap design several different reporter genes have been used in embryonic stem cells as a genetic screen to identify and mutate developmental genes in mice (Friedrich and Soriano, *Genes & Development* 5:1513–1523 (1991)). Using the ROSA gene trap design many gene trap transgenic lines have been derived that display various expression patterns in embryos at different developmental stages. Among the transgenic lines obtained have been certain promoters which appear to be ubiquitously expressed.

Gene targeting in murine embryonic stem cells has allowed the production of mice with specific gene deletions. This technique has been used in studies to try and determine the functional identification of gene products. Conventional gene knockout techniques have provided mice that inherit genetic deletions in all cell types in a regionally and temporally unrestricted manner which can lead to severe developmental defects and premature death of the knock-out animals. Several model systems have been developed which attempt to take advantage of the cell-type or tissue-type restricted expression of certain promoters operatively associated with a recombinase gene in combination with a gene of interest that has been flanked by recombinase recognition sequences. In this system the recombinase is expressed under the control of the cell-type or tissue-type specific promoter and when expressed results in the excision of the gene of interest. Because the temporal nature of cell-type and/or tissue-type specificity of the promoters is not known with any certainty results obtained with this system are suspect. Further, as these promoters are not active in all cells or in all tissues of an animal they are not-as useful for examining conditional mutations in genes.

The present invention provides methods and vector constructs which quite unexpectedly provide means to position a gene of interest under the control of an ubiquitously expressed promoter and a means to confirm the nature of the expression of the promoter sequence such that the study of these mutations in transgenic non-human organisms can be accomplished.

SUMMARY OF THE INVENTION

The present invention provides methods and vector constructs for the production of genetically engineered non-human animals which ubiquitously express a heterologous DNA segment. In one embodiment of the invention, the methods comprise transforming a pluripotent cell with a DNA construct comprising a heterologous DNA segment in which at least 100 base pairs is homologous with a DNA sequence of an ubiquitously expressed endogenous gene locus of the pluripotent cell, wherein the DNA construct becomes integrated into the gene locus by homologous recombination. Insertion of the DNA construct into the ubiquitously expressed gene locus places the DNA construct under the control of the promoter of the ubiquitously expressed gene locus and does not result in a lethal mutation.

Pluripotent cells which carry the heterologous gene inserted into and under the control of the ubiquitously expressed gene locus promoter are selected and introduced into a developing embryo, at, for example, the blastocyst or morula stage. The embryos are allowed to develop to term and offspring are selected which carry the heterologous DNA segment integrated into the ubiquitously expressed endogenous gene locus and under its promoter.

In a particularly preferred embodiment of the invention, the pluripotent cells are murine embryonic stem cells, zygotes or sperm cells, and the like. Also, in an alternative embodiment, a splice acceptor sequence is operatively associated with the heterologous DNA segment.

The methods of the present invention can be used to produce general deletor and general reporter (alternatively designated a Universal Conditional Reporter (UCR)), animal strains. In one representative embodiment of a general deletor animal, the heterologous DNA segment is a general deletor cassette comprising a gene encoding a recombinase. Optionally, a splice acceptor sequence can be associated with gene encoding the recombinase. The animal produced using the methods of the present invention ubiquitously express the recombinase in essentially all cells and all tissues throughout development. When these mice are crossed with an animal strain which has a gene of interest flanked by recombinase recognition sequences recognized by the recombinase expressed by the general deletor mouse, the gene of interest is excised from the chromosome. It is necessary for the two recombinase recognition sequences to be in the same orientation within a ubiquitously expressed endogenous gene locus. The heterologous DNA segment is positioned within the ubiquitously expressed endogenous promoter such that the reporter cassette expression is under the control of the promoter. A particularly preferred reporter is β-galactosidase.

Representative ubiquitously expressed endogenous gene loci which can be used in the methods of the present invention include ROSA26, ROSA5, ROSA23, ROSA11, and G3BP (BT5). Other loci can be determined by gene traps or other well known methods.

In an alternative embodiment of the present invention, the general deletor cassette further comprises a positive selection cassette downstream of the heterologous DNA segment. This cassette can be used in the identification of pluripotent cells which have been integrated under control of a ubiquitous promoter. Representative positive selectable markers include neo, gpt and others.

In an alternative embodiment of the general reporter cassette, the DNA stuffer sequence can comprise a promoter operatively associated with a selectable marker. The promoter can be inducible if desired. One particularly preferred promoter is PGK. Particularly preferred recombinase recognition sequences are lox and frt which are recognized by Cre and Flp recombinase, respectively.

The present invention also provides a general targeting vector cassette which comprises at least 100 base pairs of a DNA sequence homologous with an ubiquitously expressed endogenous gene locus and optionally, a negative selection cassette.

Representative gene loci which are ubiquitously expressed and can be used in the present invention include ROSA26, ROSA5, ROSA23, ROSA11 and G3BP (BTS). A particularly preferred negative selection marker is Diphtheria toxin. In a particularly preferred embodiment, 5 kb of the ROSA 26 locus is used to create a general targeting vector cassette.

In another embodiment of the present invention, a general deletor cassette is provided. The general deletor cassette comprises at least 100 base pairs of a DNA sequence homologous with an ubiquitously expressed endogenous gene locus and, optionally, a negative selection cassette. Positioned within the homologous DNA sequence is a gene encoding a recombinase. Preferred recombinase for use in the present invention are Cre and Flp. The recombinase can further be associated with an Internal Ribosome Entry Site (IRES) upstream of the recombinase gene. A particularly preferred IRES is derived from the Encephalomyocarditis virus.

In an alternative embodiment, a splice acceptor sequence is operatively associated with the recombinase gene. Downstream of the recombinase gene, the general deletor vector cassette can further include a positive selection cassette. In a preferred embodiment, the positive selection cassette comprises a promoter, such as PGK, and a positive selectable marker, such as neo or Herpes simplex virus tk. Particularly preferred ubiquitously expressed endogenous gene loci for use in the general deletor cassette are ROSA26, ROSA5, ROSA23, ROSA11, and G3BP (BT5).

In yet another embodiment of the present invention, a conditional deletor cassette is provided. The conditional deletor cassette comprises at least 100 base pairs of a DNA sequence homologous with a conditionally expressed endogenous gene locus, and optionally, a positive or negative selection cassette. Positioned within the homologous DNA sequence is a gene encoding a recombinase as described above. The recombinase can be further associated with an IRES upstream of the recombinase gene. A particularly preferred IRES is derived from the Encephalomyocarditis virus.

In an alternative embodiment, a splice acceptor sequence is operatively associated with the recombinase gene. Downstream of the recombinase gene, the general deletor vector cassette can further include a positive selection cassette. In a preferred embodiment, the positive selection cassette comprises a promoter, such as PGK, and a positive selectable marker, such as neo or Herpes simplex virus tk. A particularly preferred ubiquitously expressed endogenous gene loci for use in the conditional deletor cassette is EphA2.

In still another embodiment of the present invention, a general reporter vector cassette is provided. This cassette comprises at least 100 base pairs of a DNA sequence homologous with an ubiquitously expressed endogenous gene locus and, optionally, a negative selection cassette. Within the DNA sequence is inserted a DNA stuffer sequence flanked by two recombinase recognition sequences in the same orientation positioned upstream of a gene encoding a reporter. In one alternative embodiment of the present invention an IRES is positioned upstream of the gene encoding a reporter. In another alternative embodiment, a splice acceptor is operatively associated with the DNA stuffer sequence. The negative selection cassette is preferred to comprise a promoter operatively associated with a negatively selectable marker. A particularly preferred selectable marker is the Diphtheria toxin gene.

Preferred recombinase recognition sequences include, but are not limited to lox and Frt which are recognition sequences for the recombinases Cre and Flp, respectively.

BRIEF DESCRIPTION OF THE DRAWINGS

FIG. 1A depicts the genomic ROSA26 promoter locus. FIG. 1B depicts a map of the general targeting vector construct based on a 5 kb segment of the ROSA26 locus including a unique XbaI site and a Diphtheria toxin gene for negative selection. FIG. 1C depicts a representative general targeting vector construct with a deletor cassette comprising a recombinase gene operatively associated with an upstream splice acceptor sequence (SA), and a downstream polyadenylation sequence (bpA) with a positive selection cassette comprising a DNA segment which contains a PGK promoter, the neo gene sequence and a polyadenylation sequence. This construct is inserted into the unique XbaI site of the targeting vector. FIG. 1D depicts the representative general targeting vector with a representative reporter cassette which comprises a splice acceptor (SA) sequence operatively associated with a DNA stuffer sequence flanked by two lox sites (→) in the same orientation upstream of a reporter gene (β-galactosidase) and a polyadenylation sequence (bpA). The DNA stuffer sequence comprises a PGK promoter, a gene encoding neo and four polyadenylation sequences (4×pA).

FIG. 3A is a schematic representation of the genomic BT-5 retroviral insertion. The region of the insertion of the targeting vector is indicated. FIG. 3B is a schematic of the BT-5 targeting vector and the corresponding wildtype locus lacking the insertion. FIG. 3C is a schematic of the modified conditional reporter allele. FIG.

3D is a schematic of the conditional reporter allele following Cre-mediated excision of the Hygro cassette. (Nc) NcoI; (N) NotI; (S) SacI; (X) XhoI; (X/Sl) XhoI-SalI fusion (sites lost) restriction sites. The NotI site is derived from the phage clone and is used to linearize the vector.

Figure 4:
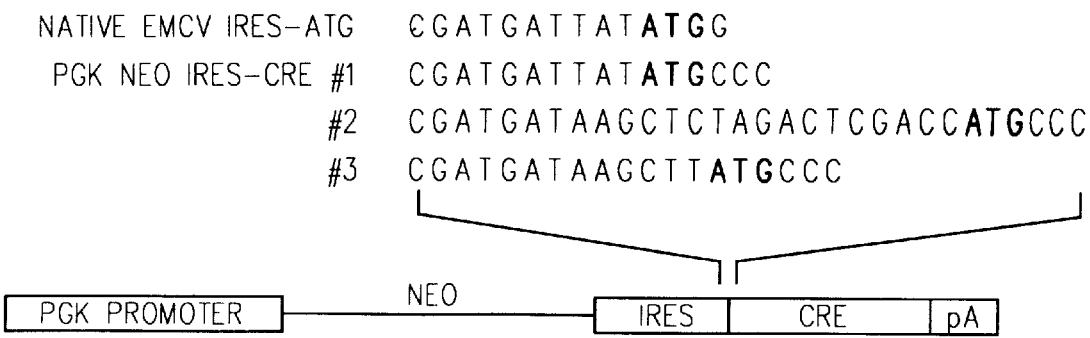

FIG. 4 depicts the IRES-Cre cassettes IRES-Cre #1, IRES-Cre #2 and IRES-Cre #3 which differ only in the nucleotide sequence between the IRES and Cre recombinase coding sequence. IRES-Cre #1 exactly duplicates the spacing and nucleotide sequence between IRES and the ATG start codon found in the EMCV genome, from which this IRES is derived. This sequence is also shown as the 'native' IRES junction sequence. IRES-Cre #2 includes a Kozak consensus sequence but the start codon is more distantly placed from the IRES than the other two cassettes. IRES-Cre #3 duplicates the junction sequence found in IRES-Geo. Each cassette was inserted as shown to generate a PGK-Neo-IRES-Cre-pA plasmid. The IRES-Cre plasmids generate a dicistronic transcript initiated from the PGK promoter and terminating at the poly A (pA) site.

FIGS. 5A through 5B depict schematic representations of the targeting vectors used to modify the EphA2 locus. FIG. 5A depicts the vector Eph-IRES-Geo, vector Eph-IRES-Cre, and the vector Eph-IRES-Cre-FRT-Hygro. In each of the three vectors, the 5'- and 3' homology is identical, only the inserted cassettes differ. The region of the EphA2 genomic locus which contains the exon encoding amino acids 1076 through 1395 and flanking intron sequence is shown. Exon sequence deleted by targeting is unshaded. The modified locus is shown on the bottom line. FIG. 5B depicts the targeted EphA2 genomic locus. (Bg) BglII; (H) HindIII; (E) EcoRI; (S) SacI; (Xb) XbaI restriction sites.

DESCRIPTION OF THE SPECIFIC EMBODIMENTS

Prior to setting forth the invention, it may be helpful to an understanding thereof to set forth definitions of certain terms to be used hereinafter.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "corresponds to" is used herein to mean that a polynucleotide sequence that shares identity to all or a portion of a reference polynucleotide sequence.

The term "complementary to" is used herein to mean that the sequence is complementary to all or a portion of a reference polynucleotide sequence.

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting transgene portion (i.e., homology region) that is substantially complementary to a reference sequence present in the target DNA (i.e., crossover target sequence). In general, targeting efficiency is optimized with the use of isogenic DNA homology clamps, although it is recognized that the presence of various recombinases may reduce the degree of sequence identity required for efficient recombination.

The term "nonhomologous sequence", as used herein, has both a general and a specific meaning; it refers generally to a sequence that is not substantially identical to a specified reference sequence, and, where no particular reference sequence is explicitly identified, it refers specifically to a sequence that is not substantially identical to a sequence of at least about 50 contiguous bases at a targeted gene locus, such as the ROSA26, ROSA5, ROSA23, ROSA11, G3BP (BT5), or EphA2 locus.

Specific hybridization is defined herein as the formation of hybrids between a targeting transgene sequence (e.g., a polynucleotide of the invention which may include substitutions, deletion, and/or additions) and a specific target DNA sequence (e.g., a ubiquitously expressed endogenous gene locus sequence), wherein a labeled targeting transgene sequence preferentially hybridizes to the target such that, for example, a single band corresponding to a restriction fragment of a genomic promoter gene locus can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume 152, Guide to Molecular Cloning Techniques* (1987), Academic Press, Inc., San Diego, Calif., which are incorporated herein by reference).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "homologuel" as used herein refers to a gene sequence that is evolutionarily and functionally related between species.

As used herein, the term "ubiquitously expressed endogenous gene locus" refers to a gene sequence encoding a non-essential protein which is expressed constitutively in essentially all cells of all tissues of an organism found in nature. As used herein, "nonessential" is intended to define a gene locus wherein insertion of a DNA sequence which disrupts or stops expression of the protein product of the ubiquitous gene locus does not result in a lethal mutation or in a mutation that results in severe developmental abnormalities.

As used herein, the term "conditionally expressed endogenous gene locus" refers to a gene sequence encoding a protein which is expressed in response to a signal at a defined time period in a cell of an organism found in nature.

As used herein, the term "targeting construct" refers to a polynucleotide which comprises: (1) at least one homology region having a sequence that is substantially identical to or substantially complementary to a sequence present in a host cell endogenous gene locus, and (2) a targeting region which becomes integrated into a host cell endogenous gene locus by homologous recombination between a targeting construct homology region and said endogenous promoter gene locus sequence. If the targeting construct is a "hit-and-run" or "in-and-out" type construct (Valancius and Smithies, *Mol. Cell. Biol.* 11:1402 (1991); Donehower et al., *Nature* 356:215 (1992); *J. NIH Res.* 3:59 (1991); which are incorporated herein by reference), the targeting region is only transiently incorporated into the endogenous promoter gene locus and is eliminated from the host genome by selection. A targeting region may comprise a sequence that is substantially homologous to an endogenous promoter gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a. sequence that substantially corresponds to, or is substantially complementary to, a predetermined endogenous gene sequence, which can include sequences flanking said gene locus. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein,. and the alternative terminology is offered for clarity, in view of the inconsistent usage of similar terms in the art. A homology clamp does not necessarily connote formation of a base-paired hybrid structure with an endogenous sequence. Endogenous gene locus sequences that substantially correspond to, or are substantially complementary to, a transgene homology region are referred to herein as "crossover target sequences" or "endogenous target sequences."

As used herein, the term "correctly targeted construct" refers to a portion of the targeting construct which is integrated within or adjacent to an endogenous crossover target sequence, such as a portion of an endogenous promoter gene locus. It is possible to generate cells having both a correctly targeted transgene(s) and an incorrectly targeted transgene(s). Cells and animals having a correctly targeted transgene(s) and/or an incorrectly targeted transgene(s) may be identified, for example, by PCR and/or Southern blot analysis of genomic DNA.

As used herein, the term "targeting region" refers to a portion of a targeting construct which becomes integrated into an endogenous chromosomal location following homologous recombination between a homology clamp and an endogenous gene locus, such as a ROSA26, ROSA5, ROSA23, ROSA11, G3BP (BT5), or EphA2 gene locus sequence. Typically, a targeting region is flanked on each side by a homology clamp, such that a double-crossover recombination between each of the homology clamps and their corresponding endogenous gene sequences results in replacement of the portion of the endogenous gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. *Bio/Technology* 10:534 (1992), incorporated herein by reference).

The term "deletor cassette" as used herein denotes a DNA segment which comprises in the 5' to 3' direction a recombinase and a polyadenylation sequence which is upstream of a positive selection cassette. An Internal Ribosome Entry Site (IRES) and/or an operatively associated splice acceptor sequence can alternatively be included upstream of the recombinase.

The term "positive selection cassette" as used herein denotes a DNA segment which comprises in the 5' to 3' direction an inducible promoter operatively associated with a gene which encodes a positive selectable marker upstream of a polyadenylation sequence.

The term "reporter cassette" as used herein denotes a DNA segment which comprises in the 5' to 3' direction a DNA stuffer sequence flanked by two recombinase recognition sequences in the same orientation, and a reporter gene operatively associated with a polyadenylation sequence. An operatively associated splice acceptor sequence can be alternatively be positioned upstream of the first recombinase recognition sequence.

The term "DNA stuffer sequence" as used herein denotes a portion of the reporter cassette comprising a DNA sequence or segment of sufficient length operatively associated with multiple polyadenylation sequences to prevent read through to DNA sequences encoding the reporter downstream of the stuffer sequence.

The term "agent" is used herein to denote a chemical compound, a mixture of chemical compounds, a biological macromolecule, or an extract made from biological materials such as bacteria, plants, fungi, or animal (particularly mammalian) cells or tissues.

An "isolated" polynucleotide or polypeptide is a polynucleotide or polypeptide which is substantially separated from other contaminants that naturally accompany it, e.g., protein, lipids, and other polynucleotide sequences. The term embraces polynucleotide sequences which have been removed or purified from their naturally-occurring environment or clone library, and include recombinant or cloned DNA isolates and chemically synthesized analogues or analogues biologically synthesized by heterologous systems.

The term "pluripotent" as used herein denotes a cell which possesses the ability to develop into certain tissues or organs, but not a complete embryo.

The term "totipotent" as used herein denotes a cell which possesses the ability to develop into any organ or a complete embryo.

DESCRIPTION OF THE SPECIFIC EMBODIMENTS

General Methods and Overview

The present invention uses the methods of gene traps to locate and characterize ubiquitously expressed endogenous gene loci and their associated promoters to express genes of interest. The genes can encode oncogenes, tumor specific antigens, or any other protein of interest. Effects of the gene product of interest can then be examined in essentially any cell or tissue of an organism. One specific example of using an ubiquitous promoter for expression of a gene of interest embodiediby present invention is the general deletor mouse. The general deletor mouse expresses a recombinase under the control of an ubiquitous promoter. Specifically, the general deletor mouse of the present invention expresses Cre recombinase under the control of ROSA26. The general deletor mouse can also include an Internal Ribosome Entry Site (IRES) upstream of the recombinase to increase the efficiency of translation of the recombinase.

In a further embodiment of the present invention, methods and materials are provided for constructing a general reporter mouse. A representative example of a general reporter mouse is provided by the present invention, wherein a reporter cassette comprising a reporter gene is positioned downstream of a DNA stuffer sequence flanked by two recombinase recognition sequences in the same orientation under the control of a ubiquitously expressed endogenous promoter. The general reporter mouse takes advantage of the ability of the recombinase to excise a DN segment located between two recombinase recognition sites in the same orientation. In the present embodiment, the DNA segment between the recombinase recognition sequences is a DNA stuffer sequence which is a DNA segment of sufficient length that when the stuffer sequence is present read through to the reporter gene is prevented. When the recombinase is present the DNA stuffer sequence is excised and the reporter gene is expressed. In a specific embodiment of the present invention, a splice acceptor sequence is operatively associated with the DNA stuffer sequence comprising a PGK promoter and the neo gene upstream of four polyadenylation sequences. The DNA stuffer sequence is flanked by two lox sites and the reporter gene is β-galactosidase.

In one embodiment of the present invention, the ubiquitous nature of the ROSA26 promoter is confirmed by crossing the general deletor mouse strain to the general reporter mouse strain. When the general reporter mice are crossed with the general deletor mice, the DNA stuffer sequence is expressed and β-galactosidase is expressed in essentially all cells and tissues of the descendent mice and in all stages of development because of the ubiquitous expression of the ROSA26-promoter. Other promoter sequences identified through gene trap systems or other methods known to the skilled artisan can also be tested for their tissue activity and/or temporal activity using the materials and methods of the present invention.

In yet another embodiment of the present invention, a conditional reporter mouse was constructed. An IRES-Cre cassette was inserted into an exon of the EphA2 gene of an ES cell line. Double heterozygous embryos having the EphA2 IRES-Cre allele and the universal conditional reporter (general deletor) locus efficiently express Cre recombinase in vivo from the EphA2 IRES-Cre allele, and it was found that the conditional reporter locus was efficiently restored in EphA2 expressing cells as early as 7.5 dpc.

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference). The generation of totipotent stem cells from fetal and adult cells and the fusion of transgenic nuclei with the cytoplasm of enucleated oocytes are accomplished using methods well known to the skilled artisan.

Oligonucleotides can be synthesized on an Applied BioSystems oligonucleotide synthesizer according to specifications provided by the manufacturer.

Gene Targeting

Gene targeting, which is a method of using homologous recombination to modify a mammalian genome, can be used to introduce changes into cultured cells. By targeting a gene of interest in pluripotent or totipotent cells, i.e., embryonic stem (ES) cells, zygote or sperm cells or totipotent cells derived from fetal or adult tissues, these changes can be introduced into the germ lines of laboratory and farm animals to study the effects of the modifications on whole organisms, among other uses. The gene targeting procedure is accomplished by introducing into cells in a culture a DNA targeting construct that has a segment homologous to a target locus and which also comprises an intended sequence modification (e.g., insertion, deletion, point mutation). The treated cells are then screened for accurate targeting to identify and isolate those which have been properly targeted. The targeting constructs are typically arranged so that they insert additional sequences, such as a positive selection marker, into coding elements of the target gene, thereby providing a method to select cells where integration of the desired sequence has occurred. Targeting constructs usually are insertion-type or replacement-type constructs (Hasty et al. *Mol. Cell. Biol.* 11:4509 (1991), incorporated herein by reference).

Targeting of a Heterologous DNA Sequence

In one embodiment, the invention encompasses methods to produce nonhuman organisms that have a heterologous gene (i.e., recombinase) under the control of an ubiquitously expressed promoter by gene targeting with-a homologous recombination targeting construct. Typically, an endogenous gene locus sequence is cloned from a genomic library, e.g., bacteriophage, or is used as a basis for producing PCR primers that flank a region that will be used as a homology clamp in a targeting construct. The PCR primers are then used to amplify, by high fidelity PCR amplification (Mattila et al., *Nucleic Acids Res.* 19:4967 (1991); Eckert, K. A. and Kunkel, T. A., *PCR Methods and Applications* 1:17 (1991); U.S. Pat. No. 4,683,202, which are incorporated herein by reference), a genomic sequence from a genomic clone library or from a preparation of genomic DNA, preferably from the strain of nonhuman animal that is to be targeted with the targeting construct. The amplified DNA is then used as a homology clamp and/or targeting region. Thus, homology clamps for targeting essentially any endogenous gene locus may be readily produced on the basis of nucleotide sequence information available in the art and/or by routine cloning. General principles regarding the construction of targeting constructs and selection methods are reviewed in Bradley et al., *Bio/Technology* 10:534 (1992), incorporated herein by reference.

Targeting constructs can be transferred into pluripotent stem cells, such as murine embryonal stem cells, wherein the targeting constructs homologously recombine with a portion of an endogenous promoter gene locus and create mutation (s) (i.e., insertions, deletions, rearrangements, sequence replacements, and/or point mutations).

In another embodiment of the invention the gene of interest can be targeted by other means known to the skilled artisan including gene trap systems. The method of targeting the heterologous DNA sequence to the gene locus is not critical and any method used is intended to be encompassed by the present invention.

A preferred method of the invention is to insert, by targeted homologous recombination, either a general deletor construct containing a heterologous gene under the control of the promoter locus or a general reporter construct under the control of a separate promoter locus. In one specific embodiment, a DNA sequence encoding a recombinase has been inserted. In a second embodiment, a DNA stuffer sequence flanked by two recombinase recognition sequences upstream of a reporter gene have been inserted.

As a specific example, a targeting construct can homologously recombine with the ubiquitously expressed endogenous ROSA26 promoter gene locus and insert a desired gene sequence into the ROSA26 promoter gene locus such that the inserted gene is under the control of the ROSA26 promoter locus. In one embodiment a heterologous recombinase, i.e., Cre, is inserted into the ROSA26 locus to form a general deletor construct. In another embodiment a general reporter construct is generated which contains a splice acceptor site operatively associated with a gene of interest flanked by recombinase recognition sequences positioned upstream of a reporter gene. In still another embodiment, rather than inserting the Cre coding sequence in-frame within the endogenous locus, a novel Internal Ribosomal Entry Site (IRES) Cre recombinase cassette, which permits the expression of Cre from any targeted exon insertion is provided.

In another specific embodiment of the present invention a deletor cassette has been inserted into a conditionally expressed endogenous gene. Specifically the IRES-Cre deletor cassette has been inserted under the control of the endogenous regulatory elements of the EphA2 gene, a member of the Eph family of receptor tyrosine kinases formerly referred to as eck. (Ganju et al., *Oncogene* 9:1613–1624 (1994); Ruiz and Robertson, *Mech. Dev.* 46:87–100 (1994); and Chen et al., *Oncogene* 12:979–88 (1996)). Insertion of the deletor cassette under the control of the regulatory elements of a conditionally expressed gene allows the marking of cells derived from a particular event or signal which induces the expression of the recombinase and subsequent modification of the reporter cassette through development.

Targeting Constructs

Several gene targeting techniques have been described, including but not limited to: co-electroporation, "hit-and-run", single-crossover integration, and double-crossover recombination (Bradley et al., *Bio/Technology* 10: 534 (1992), incorporated herein by reference). The invention can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example, and not by way of limitation, a specific embodiment of a targeting construct comprises, in order: (1) a first homology clamp having a sequence substantially identical to a sequence within about 3 kilobases downstream (i.e., in the direction of the functional reading frame of the promoter gene locus) of the promoter region of the promoter gene locus, (2) an insertion sequence comprising a splice acceptor sequence, a gene sequence of interest, such a recombinase, (3) a second homology clamp having a sequence substantially identical to a sequence within the ubiquitously expressed gene locus, and (4) a negative selection cassette, e.g., one comprising a-Diphtheria toxin gene with the PGK promoter driving transcription. Such a targeting construct is suitable for double-crossover replacement recombination which inserts a desired construct into the ubiquitously expressed endogenous promoter gene locus having the recombinase cassette.

Similarly, the targeting construct for the general reporter construct contains the same elements of the general deletor construct except instead of the recombinase gene cassette, the cassette comprises a DNA stuffer sequence containing a gene of interest flanked by two sites recognized by the heterologous recombinase of the deletor construct, and a reporter gene. Alternatively, a splice acceptor can be operatively associated with the DNA stuffer sequence.

Targeting constructs of the invention comprise at least one homology clamp linked in polynucleotide linkage (i.e., by phosphodiester bonds) to a targeting region. A homology clamp has a sequence which substantially corresponds to, or is substantially complementary to, a predetermined endogenous promoter gene locus of a nonhuman host organism.

Although no lower or upper size boundaries for recombinogenic homology clamps for gene targeting have been conclusively determined in the art, the best mode for homology clamps is believed to be in the range between about 50 base pairs and several tens of kilobases. Consequently, targeting constructs are generally at least about 50 to 100 nucleotides long, preferably at least about 250 to 500 nucleotides long, more preferably at least about 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred, with one preferred embodiment having a first homology region of about 7 kilobases flanking one side of a replacement region and a second homology region of about 1 kilobase flanking the other side of said replacement region. The length of homology (i.e., substantial identity) for a homology region may be selected at the discretion of the practitioner on the basis of the sequence composition and complexity of the predetermined endogenous promoter gene locus target sequence(s) and guidance provided in the art (Hasty et al., *Mol. Cell. Biol.* 11:5586 (1991); Shulman et al., *Mol. Cell. Biol.* 10:4466 (1990), which are incorporated herein by reference). In targeting constructs, such homology regions typically flank the replacement region, which is a region of the targeting construct that is to undergo replacement with the targeted ubiquitously expressed gene locus (Berinstein et al. *Mol. Cell. Biol.* 12:360 (1992), which is incorporated herein by reference). Thus, a segment of the targeting construct flanked by homology regions can replace a segment of a gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Without wishing to be bound by any particular theory of homologous recombination or gene conversion, it is believed that in such a double-crossover replacement recombination, a first homologous recombination (e.g., strand exchange, strand pairing, strand scission, strand ligation) between a first targeting construct homology region and a first endogenous promoter gene locus sequence is accompanied by a second homologous recombination between a second targeting construct homology region and a second endogenous promoter gene locus sequence, thereby resulting in the portion of the targeting construct that was located between the two homology regions replacing the portion of the endogenous promoter gene locus sequence that was located between the first and second endogenous gene sequences. For this reason, homology regions are generally used in the same orientation (i.e., the upstream direction is the same for each homology region of a transgene to avoid rearrangements). Double-crossover replacement recombination thus can be used to insert a portion of an endogenous promoter gene locus and concomitantly transfer a nonhomologous portion (e.g., a Cre gene expression cassette, a IRES-Cre gene expression cassette, or a neo gene operatively linked with a reporter gene) into the corresponding chromosomal location. Upstream and/or downstream from the nonhomologous portion may be a gene which provides for identification of whether a double-crossover homologous recombination has occurred; such a gene can be the Diphtheria toxin gene DTA which may be used for negative selection.

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker. Selectable markers typically are also be used for hit-and-run targeting constructs and selection schemes (Valancius and Smithies, supra, incorporated herein by reference). Preferred constructs of the invention encode and express a selectable drug resistance marker and/or a Diphtheria toxin gene. Suitable drug resistance genes include, for example: gpt (xanthine-guanine phospho-ribosyltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg, *Proc. Natl. Acad. Sci.* (*U.S.A.*) 78:2072 (1981); Southern and Berg, *J. Mol. Appl. Genet.* 1:327 (1982); which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. In the present invention, such negative selection employs an expression cassette encoding the Diphtheria toxin gene DTA, but can also include the herpes simplex virus thymidine kinase gene (HSV tk) positioned in the transgene so that it should integrate only by nonhomologous recombination. Such positioning generally is accomplished by linking the negative selection cassette distal to the recombinogenic homology regions so that double-crossover replacement recombination of the homology regions transfers the positive selection expression cassette to a chromosomal location but does not transfer the negative selection gene to a chromosomal location. If the HSV tk is used a nucleoside analog, such as gancyclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme is typically used (Mansour et al. (1988) op. cit., incorporated herein by reference). Positive-negative selection involves the use of two active selection cassettes: (1) a positive selection cassette (e.g., the neo gene), that can be stably expressed following either random integration or homologous targeting, and (2) a negative selection cassette (e.g., the Diphtheria toxin gene), that can only be stably expressed following random integration, and cannot be expressed after correctly targeted double-crossover homologous recombination. By combining both positive and negative selection steps, host cells having the correctly targeted homologous recombination between the transgene and the ubiquitously expressed endogenous promoter gene locus can be obtained.

Generally, targeting constructs for the general reporter vector of the invention preferably include: (1) a desired gene, i.e., a positive selection expression cassette, flanked by two sites recognized by the recombinase of the general deletor construct operatively associated with a reporter gene flanked by two homology regions that are substantially identical to host cell endogenous promoter gene locus sequences, and (2) a distal negative selection expression cassette. However, targeting constructs which include only a positive selection expression cassette can also be used. More typically, the targeting transgene will also contain a negative selection expression cassette which includes a Diphtheria toxin gene linked downstream of a PGK promoter.

It is preferred that targeting constructs of the invention have homology regions that are highly homologous to the predetermined target. endogenous DNA sequence(s), preferably isogenic (i.e., identical sequence). Isogenic or nearly isogenic sequences may be obtained by genomic cloning or high-fidelity PCR amplification of genomic DNA from the strain of nonhuman mammals which are. the source of the pluripotent cells, i.e., embryonic stem cells, used in the gene targeting procedure. Therefore, both homology region length and the degree of sequence homology can only be determined with reference to a particular predetermined sequence, but homology regions generally must be at least about 50 nucleotides long and must also substantially correspond or be substantially complementary to a predetermined endogenous target sequence. Preferably, a homology region is at least about 100 nucleotides long and is identical to or complementary to a predetermined target sequence in or flanking a promoter gene locus. If it is desired that correctly targeted homologous recombinants are generated at high efficiency, it is preferable that at least one homology region is isogenic (i.e., has exact sequence identity with the crossover target sequence(s) of the promoter gene locus), and is more preferred that isogenic homology regions flank the exogenous targeting construct sequence that is to replace the targeted promoter gene locus sequence.

Generally, any predetermined endogenous gene locus can be altered by homologous recombination (which includes gene insertion) with a targeting transgene that has at least one homology region which substantially corresponds to or is substantially complementary to a predetermined endogenous gene locus sequence in a mammalian cell having the same predetermined endogenous gene locus sequence. Particularly preferred endogenous gene loci include, but are not limited to, ROSA26, ROSA5, ROSA23, ROSA11, G3BP (BT5), and EphA2.

The operation of a promoter may vary depending on its location in the genome. Thus, a regulated promoter may operate differently from how it does in its normal location, e.g., it may become fully or partially constitutive.

It is preferred to have the DNA sequence linked to and situated at a distance from the promoter corresponding to the distance at which the promoter is normally most effective so as to ensure sufficient transcriptional activity. This distance should be within about 1000 nucleotides, preferably within about 500 nucleotides and more preferably within about 300 nucleotides of the translation initiation codon.

At the 3' end of the coding sequence, operably linked segments may also be included. Thus, it would be optimum to have a 3' untranslated region containing the polyadenylation site and any relevant transcription termination sites. A 31 sequence of less than about 1000 nucleotides is sufficient, about 500 preferred and about 300, or the length of the 3' untranslated tail of the endogenous sequence is more preferred.

Typically, a targeting transgene comprises a portion having a sequence that is not present in the preselected targeted endogenous gene locus sequence(s) (i.e., a nonhomologous portion) which may be as small as a single mismatched nucleotide or may span up to about several kilobases or more of nonhomologous sequence. Substitutions, additions, and deletions may be as small as 1 nucleotide or may range up to about 2 to 10 kilobases or more.

In one embodiment of the invention a targeting transgene of the general deletor construct is transferred into pluripotent stem cell line which can be used to generate a transgenic nonhuman deletor animal following injection into a host blastocyst. In a second embodiment of the invention, a targeting transgene of the general reporter construct is transferred into a second pluripotent cell which can be used to generate a transgenic non-human reporter animal following insertion into a developing host embryo. In a preferred embodiment of the invention, a general deletor targeting construct containing a heterologous recombinase (e.g., Cre) and a negative (e.g., Diphtheria toxin gene, DTA) selection expression cassette. The recombinase targeting transgene is transferred into mouse ES cells (e.g., by electroporation) under conditions suitable for the continued viability of the electroporated ES cells. The electroporated ES cells are cultured under selective conditions for negative selection. Selected cells are then verified as having the correctly targeted transgene recombination by PCR analysis according to standard PCR or Southern blotting methods known in the art (U.S. Pat. No. 4,683,202; Erlich et al., Science 252:1643 (1991), which are incorporated herein by reference). Correctly targeted ES cells are then transferred into suitable blastocyst hosts for generation of chimeric transgenic animals according to methods known in the art (Capecchi, M. (1989) op. cit., incorporated herein by reference).

In another preferred embodiment of the invention a general reporter targeting construct containing a desired gene flanked by lox sites (e.g., neo) and a negative (e.g., Diphtheria toxin gene, DTA) selection expression cassette. The recombinase targeting transgene is transferred into mouse ES cells (e.g., by electroporation) under conditions suitable for the continued viability of the electroporated ES cells. The electroporated ES cells are cultured under selective conditions for positive selection (e.g., a selective concentration of G418), and optionally are cultured under selective conditions for negative selection, either simultaneously or sequentially. Selected cells are then verified as having the correctly targeted transgene recombination as described above.

Briefly, the invention involves in one example, the insertion of a heterologous recombinase gene to form a general deletor organism using a targeting construct based on the introduction of various recombinase genes at the ROSA26 promoter locus, as a means to achieve ubiquitous expression of the recombinase in mice. The invention also comprises construction of a second strain of organism which is a general reporter mouse strain. The reporter mice exploit the ability of the Cre recombinase to. specifically delete sequences flanked by lox sites. In a specific embodiment of the present invention, the ROSA26 promoter is engineered to express a detectable marker only following expression of Cre recombinase, as its expression is otherwise prevented by a stuffer DNA fragment containing a selectable neo expression cassette. When the general deletor mouse is crossed with the general reporter mouse containing a desired gene sequence flanked by lox sites, Cre expression results in the deletion of the lox flanked gene sequence in the, germ line. Such a mouse line will be useful to remove a selectable marker or to engineer a new allele carrying a small mutation in a gene from an initial founder stock colony.

Targeting transgenes can be transferred to host cells by any suitable technique, including microinjection, electroporation, lipofection, biolistics, calcium phosphate precipitation, and viral-based vectors, among others. Other methods used to transform mammalian cells include the use of Polybrene, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference).

It is preferable to use a transfection technique with linearized transgenes containing only modified target gene sequence(s) and without vector sequences. The modified gene site is such that a homologous recombinant between the exogenous targeting construct and the endogenous DNA target sequence can be identified by using carefully chosen primers and PCR or by Southern blot analysis, followed by analysis to detect if PCR products or Southern blot bands specific to the desired targeted event are present (Erlich et al., (1991) op.cit.), which is incorporated herein by reference). Several studies have already used PCR to successfully identify the desired transfected cell lines (Zimmer and Gruss, *Nature* 338: 150 (1989); Mouellic et al., *Proc. Natl. Acad. Sci.* (*U.S.A.*) 87:4712 (1990); Shesely et al., *Proc. Natl. Acad. Sci. USA* 88: 4294 (1991), which are incorporated herein by reference). This approach is very effective when the number of cells receiving exogenous targeting transgene(s) is high (i.e., with electroporation or with liposomes) and the treated cell populations are allowed to expand (Capecchi, M. (1989) op. cit., incorporated herein by reference).

For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, *Cell* 62:1073–1085 (1990)) essentially as described (Robertson, E. J. (1987) in *Teratocarcinomas and Embryonic Stem Cells: A Practical Approach.* E. J. Robertson, ed. (Oxford: IRL Press), p. 71–112) may be used for homologous gene targeting. Other suitable ES lines include, but are not limited to, the E14 line (Hooper et al., *Nature* 326:292–295 (1987)), the D3 line (Doetschman et al., *J. Embryol. Exp. Morph.* 87:27–45 (1985)), the CCE line (Robertson et al., *Nature* 323:445–448 (1986)), the AK-7 line (Zhuang et al., *Cell* 77:875–884 (1994) which is incorporated by reference herein). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having either the recombinase or reporter loci and are backcrossed and screened for the presence of the correctly targeted transgene(s) by PCR or Southern blot analysis on tail biopsy DNA of offspring so as to identify transgenic mice heterozygous for either the recombinase or reporter locus/loci.

The following examples are offered by way of illustration, not by way of limitation.

EXAMPLE I

In this example ubiquitous reporter gene activity has been produced by random retroviral gene trapping in embryonic stem cells. The mouse strain which demonstrates ubiquitous expression of a reporter gene integrated in its tissues has been designated ROSA26. The general utility of this strain for chimera and transplant studies has been demonstrated in this example by bone marrow transfer experiments. Also, the region into which the reporter gene has integrated has been characterized in this example.

MATERIALS AND METHODS

Genotyping and Xgal Staining. Mice were maintained on C57BL/6×129Sv, 129Sv congenic, and C57BL/6J congenic backgrounds, and are available from the Induced Mutant Resource at the Jackson Laboratory. Xgal staining was carried out as previously described (MacGregor et al., *Development* 121:1487–1496 (1995)). Mouse genomic DNA was digested with StuI and electrophoresed on a 0.7% agarose gel. The gel was blotted onto Hybond N$^+$ and probed with the 5' RACE product. The probe hybridizes to approximately 7 kb and 12 kb bands, corresponding to the wild type and mutant alleles, respectively. PCR genotyping was done using the following 3 primers: 5'-ggc tta aag gct aac ctg atg tg-3' (SEQ ID NO: 1); 5'-gcg aag agt ttg tcc tca acc-3' (SEQ ID NO: 2); and 5'-gga gcg gga gaa atg gat atg-3' (SEQ ID NO: 3). The sizes of the wild type and mutant fragments were 374 bp and 1146 bp, respectively.

Multiparameter FACS-Gal Analysis. Mononuclear cells prepared from spleen, bone marrow, thymus and peritoneal cavity were first subjected to hypotonic loading with fluorescein di-β-D-galactopyranoside (FDG), returned to isotonicity at 4° C. and stained with antibodies for specific surface determinants as previously described (Kerr et al., *Cold Spring Harbor Symp. Ouant. Biol.* 54:767–776 (1989)). For antibody staining of cells "loaded" with .FDG the cells were kept at 4° C. at all steps in the staining procedure, including centrifugation in pre-chilled rotors and adapters. Antibody stains and the staining medium used in the procedure were also kept on ice throughout the duration of the procedure.

5' and 3' RACE, cDNA and Genomic Cloning. 5' RACE was carried out according to Chen (Chen, Z., *Trends in Genetics* 12:87–88 (1996)) and 3' RACE was done as described by Frohman (Frohman, M. A. "*PCR Methods and Applications*" 4:S40–S58 (1994)). Plasmids pR26-10 and pR26-9 contain subclones of 3' RACE products from transcripts 1 and 2, respectively. The pR26-10 insert was used to identify 8 clones from an E11.5 oligo dT primed mouse embryo cDNA library. The pR26-9 insert was used to probe the E11.5 and an E16.5 mouse oligo dT primed embryo cDNA library. A single clone was identified in the E16.5 library. The same probe was used to screen a mouse random primed embryonic stem (ES) cell cDNA library and 8 transcript antisense (AS) clones were obtained. The longest of these was used to reprobe the ES cell cDNA library and 25 additional clones were obtained.

The pR26-10 insert was also used to screen a mouse 129Sv genomic library. Three clones were obtained and one contained genomic sequence on both the 5' and 3' ends of the ROSAβgeo integration site. A partial EcoRI fragment of this clone (G19) was subcloned into the EcoRI site of pBSII KS (Stratagene) resulting in plasmid pR26G19 which was used to map the ROSA26 region. The 5' end of the ROSAβgeo insertion was amplified by PCR from ROSA26 homozygous mouse DNA using an exon 1 specific primer (r265'f, 5'-tgc gtt tgc ggg gat gg-3'; SEQ ID NO: 4) and a splice acceptor (SA) specific primer (SAR, 5'-gcg aag agt ttg tcc tca ac-3'; SEQ ID NO: 5).

The sequences for the promoter region (Table 1, SEQ ID NO: 6) and transcripts 1 (Table 2; SEQ ID NO: 7), 2 (Table 3; SEQ ID NO: 8), and AS (Table 4; SEQ ID NO: 9 and Table 5; SEQ ID NO: 10) have been submitted to GenBank and can be accessed using the following numbers: U83173, U83174, U83175, and U83176, respectively.

TABLE 1

DNA Sequence of ROSA26 Gene Locus Promoter

| | | | | | |
|---|---|---|---|---|---|
| ctcgagttag | gcccaacgcg | gcgccacggc | gtttcctggc | cgggaatggc | ccgtacccgt |
| gaggtggggg | tggggggcag | aaaaggcgga | gcgagcccga | ggcggggagg | gggagggcca |
| ggggcggagg | gggccggcac | tactgtgttg | gcggactggc | gggactaggg | ctgcgtgagt |
| ctctgagcgc | aggcgggcgg | cggccgcccc | tcccccggcg | gcggcagcgg | cggcagcggc |
| ggcagctcac | tcagcccgct | gcccgagcgg | aaacgccact | gaccgcacgg | ggattcccag |
| tgccggcgcc | aggggcacgc | gggacacgcg | ccctcccgcc | gcgccattgg | cctctccgcc |
| caccgcccca | cacttattgg | ccggtgcgcc | gccaatcagc | ggaggctgcc | ggggccgcct |
| aaagaagagg | ctgtgctttg | gggctccggc | tcctcagaga | gcctcggcta | ggtaggggat |
| cgggactctg | gcgggagggc | ggcttggtgc | gtttgcgggg | atgggcggcc | gcgg |

TABLE 2

Nucleotide Sequence of ROSA26 (Transcript 1)

| | | | | | |
|---|---|---|---|---|---|
| ggctcctcag | agagcctcgg | ctaggtaggg | gatcgggact | ctggcgggag | ggcggcttgg |
| tgcgtttgcg | gggatgggcg | gccgcggcag | gccctccgag | cgtggtggag | ccgttctgtg |
| agacagccgg | atcattcctt | gaggacagga | cagtgcttgt | ttaaggctat | atttctgctg |
| tctgagcagc | aacaggtctt | cgagatcaac | atgatgttca | taatcccaag | atgttgccat |
| ttatgttctc | agaagcaagc | agaggcatga | tggtcagtga | cagtaatgtc | actgtgttaa |
| atgttgctat | gcagtttgga | tttttctaat | gtagtgtagg | tagaacatat | gtgttctgta |
| tgaattaaac | tcttaagtta | caccttgtat | aatccatgca | atgtgttatg | caattaccat |
| tttaagtatt | gtagcttct | ttgtatgtga | ggataaaggt | gtttgtcata | aaatgttttg |
| aacatttccc | caaagttcca | aattataaaa | ccacaacgtt | agaacttatt | tatgaacaat |
| ggttgtagtt | tcatgctttt | aaaatgctta | attattcaat | taacaccgtt | tgtgttataa |
| tatatataaa | actgacatgt | agaagtgttt | gtccagaaca | tttcttaaat | gtatactgtc |
| tttagagagt | ttaatatagc | atgtctttg | caacatacta | acttttgtgt | tggtcgagc |
| aatattgtgt | agtcatttg | aaaggagtca | tttcaatgag | tgtcagattg | ttttgaatgt |
| tattgaacat | tttaaatgca | gacttgttcg | tgttttagaa | agcaaaactg | tcagaagctt |
| tgaactagaa | attaaaaagc | tgaagtattt | cagaagggaa | ataagctact | tgctgtatta |
| gttgaaggaa | agtgtaatag | cttagaaaat | ttaaaaccat | atagttgtca | ttgctgaata |
| tctggcagat | gaaaagaaat | actcagtggt | tcttttgagc | aatataacag | cttgttatat |
| taaaaatttt | ccccacagat | ataaactcta | atctataact | cataaatgtt | acaaatggat |
| gaagcttaca | aatgtggctt | gacttgtcac | tgtgcttgtt | ttagttatgt | gaaagtttgg |
| caataaacct | atgtcctaaa | t | | | |

TABLE 3

Nucleotide Sequence of ROSA26 (Transcript 2)

| | | | | | |
|---|---|---|---|---|---|
| ctaggtaggg | gatcgggact | ctggcgggag | ggcggcttgg | tgcgtttgcg | gggatgggcg |
| gccgcggcag | gccctccgag | cgtggtggag | ccgttctgtg | agacagccgg | atcattcctt |
| gaggacagga | cagtgcttgt | ttaaggctat | atttctgctg | tctgagcagc | aacaggtctt |
| cgagatcaac | atgatgttca | taatcccaag | atgttgccat | ttatgttctc | agaagcaagc |
| agaggcatga | tggagggtct | cttccttcat | cttgatctga | aggatgaaca | aaggcttgag |
| cagtgcgctt | tagaagataa | actgcagcat | gaaggccccc | gatgttcacc | cagactacat |
| ggacctttcg | ccacacatgt | cccattccag | ataaggcctg | gcacacacaa | aa |

TABLE 4

Nucleotide Sequence of ROSA26 (Antisense Region)

| | | | | | |
|---|---|---|---|---|---|
| tcggcttccg | gcggcgtgct | cgcggtgcgg | agaccggaag | ggtctgtgct | tgctgccgag |
| actgttggtc | cttttagaaa | catctccatc | atgtcttgtg | acactcaaga | agctaccaga |
| gagtgcctgg | gtatgaacct | tgatggcaac | aaagagcctg | tgtcgctggt | agaaagcggc |
| gtcagaagtg | agtcggagca | tctccaagtc | actattggag | ccactgtacc | cactggcttt |
| gaacaaacgg | ctgcggggga | agtgagagag | aaactgaagt | cggcctgcag | aatcagcaaa |
| gaccgcggaa | agatctattt | tgatattgca | gtggaaagtc | tggctcaggt | tcattgtctg |
| agatcagttg | ataacttgtt | tgtggttgtt | caggagttta | aagattacca | gttcaaagat |
| acgaaggaag | aagttctaag | agactttgaa | gaactggctg | gaaaactccc | atggtcagac |
| cctttaaaag | tctgcaaat | taacaccact | ttcaagaaga | agaaagcaaa | gcgcagaaag |
| gcaaatcaga | gtgcaggtaa | agagaaggct | gactgtggac | aaggagacaa | agcagatgag |
| aaagatggta | agaaaaagca | tgccagcagc | acttcagatt | cacatatctt | ggactattat |
| gaaatccag | ccatcaaaga | agagatca | acctagtag | gtgatgtctt | gtcgtcttgc |
| aaagatgaaa | ctggtcaaag | cttaagagaa | gaaactgaac | cacaggtaca | gaagtttaga |
| gtcacctgca | acagagcagg | agagaaacat | tgctttacct | ccaatgaggc | tgcgagagat |
| tttggggtg | ctattcaaga | gtactttaag | tggaaggctg | atatgaccaa | ctttgatgta |
| gaggttctcc | tgaacatcca | tgataatgaa | gtcattgttg | ctattgcact | gacagaagag |

TABLE 4-continued

Nucleotide Sequence of ROSA26 (Antisense Region)

| | | | | | |
|---|---|---|---|---|---|
| agtctccatc | gcagaaatat | tacacatttt | ggacctacaa | ctcttaggtc | aactcttgcc |
| tatgggatgc | tcaggctctg | tgaacctaag | cctactgatg | taatagtgga | cccaatgtgt |
| ggaacagggg | caataccaat | agagggggct | actgagtggt | ctcactgtta | ccatattgct |
| ggggacaata | acccactggc | agtgaacaga | gcagcaaata | acatctcatc | tctattgact |
| aagagccaga | ttaaagatgg | aaaaacaacc | tggggtttgc | ccattgatgc | tgttcagtgg |
| gatatctgca | acctcccact | gagaactgct | tctgtggata | ttattgtaac | agatatgcca |
| tttggaaaaa | ggatgggatc | caagaagaga | aattggaatc | tctatccagc | ttgccttcgg |
| gaaatgagcc | gtgtctgtag | accagggaca | ggcagagctg | tactgcttac | tcaggacaag |
| tttgttcatc | cttcagatca | agatgaagga | agagaccctc | cttggtaaag | aaaagagtga |
| aaatgttta | ccaaggcctt | atctggaatg | ggacatgtgt | ggcgaaaggt | ccatgtagtc |
| tttgttcatc | cttcagatca | agatgaagga | agagaccctc | cttggtaaag | aaaagagtga |
| agacaactta | ttaatatttg | tagttcctaa | cactggaaat | atcagcataa | agaacttgct |
| ttgggagaaa | aatagcagaa | aagtaactta | cagtacaggt | tacactgctt | gaccactcca |
| gaatgcttga | tttctagcaa | ggtgattgta | atggtatttc | ttaagaagcc | tacactgctt |
| ggcttctaag | tgtcagaaca | ctttaggcca | tattctattg | cttgtgcaac | ctactgtttt |
| atggtctaaa | ttctttgtat | catctcagaa | gcagaagtat | cccttaagat | ctacagtttt |
| atcatctgct | ttaaaataaa | tatacaacct | aaacagagca | aaaaaaaaaa | aaaa |

TABLE 5

Amino Acid Sequence of ROSA26 (Antisense Region)

MSCDTQEATRECLGMNLDGNKEPVSLVESGVRSESEHLQVTIGA

TVPTGFEQTAAGEVREKLKSACRISKDRGKIYFDIAVESLAQVHCLRSVDNLFVVVQE

FKDYQFKDTKEEVLRDFEELAGKLPWSDPLKVWQINTTFKKKKAKRRKANQSAGKEKA

DCGQGDKADEKDGKKKHASSTSDSHILDYYENPAIKEEISTLVGDVLSSCKDETGQSL

REETEPQVQKFRVTCNRAGEKHCFTSNEAARDFGGAIQEYFKWKADMTNFDVEVLLNI

HDNEVIVAIALTEESLHRRNITHFGPTTLRSTLAYGMLRLCEPKPTDVIVDPMCGTGA

IPIEGATEWSHCYHIAGDNNPLAVNRAANNISSLLTKSQIKDGKTTWGLPIDAVQWDI

CNLPLRTASVDIIVTDMPFGKRMGSKKRNWNLYPACLREMSRVCRPGTGRAVLLTQDK

KCFTKALSGMGHVVRKVHVVVVNIGGLHAAVYLLKRTAQAFVHPSDQDEGRDPPW

Northern Blotting. Northern blots were carried out using 20 μg of total RNA per lane on a 1.4% agarose gel. The EcoRI-HindIII fragment of pR26-10 (nucleotide (nt) 98–1162 of transcript 1; SEQ ID NO: 7) was used as a probe for transcript 1 while the XhoI fragment of transcript AS cDNA-1 (nt 887 through approximately nt 1600 of transcript AS; SEQ ID NO: 9) was used as a probe for transcript AS. RT-PCR. The RT-PCR reactions were carried out using kidney total RNA and the 3' RACE protocol (Frohman, M. A. *"PCR Methods and Applications"* 4:S40–S58 (1994)). The primers for detecting transcript 1 are R26GSP0 and $Q_0$ followed by Rosa263' (5'-gcc gtt ctg tga gac ag-3'; SEQ ID NO: 11) and 575–695R (5'-aaa tgt tct gga caa aca ctt c-3'; SEQ ID NO: 12), and result in a 533 bp product. Primers for detecting transcript 2 are R26GSP0 and $Q_0$ followed by R26B (5'-cgc act gct caa gcc ttt gtt c-3'; SEQ ID NO: 13) and Rosa263', and result in a 217 base pair product. Primers for detecting transcript AS are R26alt2 (5'-taa ctc cag ttc tag ggg g-3'; SEQ ID NO: 14) and $Q_0$ followed by R26B and Rosa26i2-F1 (5'-ggt caa gca gtg taa cct G-3'; SEQ ID NO: 15), and result in a 188 bp product.

Testing of Promoter Fragments. Several putative promoter fragments 5' of exon 1 of transcripts 1 and 2 were placed upstream of βgal. Since a Kozak ATG exists in exon 1 just 5' of the Not I site that could affect translation of βgal, it was mutagenized to a BamHI site using primer rosa265'-mutR (5'-cgg atc ccc gca aac gca cca a-3'; SEQ ID NO: 16). These fragments were subcloned into the HindIII site of pSAβgal-PGKneo (Friedrich et al., *Genes and Development* 5:1513–1523 (1991)) after the removal of the splice acceptor (SA) site and the resulting constructs were electroporated into embryonic stem (ES) cells. Following selection with G418, resistant colonies were pooled (approximately 1000/construct), grown up and used to produce cell extracts. βgal activity was measured using o-Nitrophenyl-β-D-galactopyranoside (ONPG) as a substrate (Sambrook et al., *Molecular Cloning: A Laboratory Manual* (Cold Spring Harbor Laboratory Press) (1989)) and BioRad (Hercules, Calif.) protein assays were done on each extract to determine the protein concentrations.

RESULTS

The Trapped Gene is Expressed Ubiquitously

The ROSA26 mutant line was produced by infection of murine embryonic stem ES cells with the ROSAβgeo retrovirus (Friedrich et al., *Genes and Development* 5:1513–1523 (1991)). Heterozygotes did not display an overt phenotype and were recovered in expected numbers from heterozygous fathers (471, N=147) or mothers (46%, N=84) bred to wild type. Significantly fewer than expected homozygotes were recovered from crosses between two heterozygous parents (11%, N=114; p<0.01 $\chi^2$ test), but these homozygotes did not display an overt phenotype and were fertile. ROSA26 was one of several gene trap lines which exhibited widespread βgal expression (Friedrich et al., Supra), starting at the morula-blastocyst stage. Examination of serial sections through (embryonic day) E9.5 embryos demonstrated blue staining in all cells (Chen et al., Genes & Development 9:686–699 (1995)). As most tissues are formed by birth, expression in neonates was also examined. Ubiquitous staining was found in the following tissues: brain, bone marrow, cartilage, heart, intestine, kidney, liver, lung, pancreas, muscle (skeletal and smooth), skin (dermis and epidermis), spleen, submandibular gland, thymus, trachea and urinary bladder. Because the staining was superficial even when tissues were cut open, histological sections were examined only in layers that contained stained cells to confirm ubiquitous staining. Frozen sections generally provided much weaker signals than paraffin sections. Moreover, ubiquitous expression has been found in adult testis, and the brain exhibits ubiquitous βgal expression except for olfactory bulb granule cells (Zambrowicz et al., Proc. Natl. Acad. Sci. USA 94:3789–3794 (1997)).

βgalactosidase Expression in the Hematolymphoid Compartment and Hematopoietic Transplantation.

Nucleated cells in spleens from ROSA26 and two other strains, ROSA11 and ROSA27, that also exhibited apparently ubiquitous βgeo expression in (day 12) E12 embryos (Friedrich et al., Genes and Development 5:1513–1523 (1991)), were analyzed for expression of βgal by multiparameter FACS-Gal analysis. Only ROSA26 showed ubiquitous expression in the nucleated cells in spleen. In addition, all major hematolymphoid lineages express βgal ubiquitously. Ubiquitous expression of βgal was found in B-cells (B220$^+$), T-cells (CD5$^+$) and myeloid cells (Mac-1$^+$) in the spleen and their relative proportion was comparable to that found in normal animals (e.g. C57BL/6J), indicating that development of these various lineages is not impaired in mice homozygous for the gene-trap integration. When other hematolymphoid tissues were analyzed, ubiquitous expression was also observed in nucleated cells, including bone marrow (BM), thymus (Thy), peritoneal cavity and peripheral blood. Because nucleated erythrocyte progenitors are present in BM cell suspensions, they should also express βgal since all BM cells express βgal in ROSA26, whereas non-nucleated definitive erythrocytes present in peripheral blood of ROSA26 mice do not express βgal. Lack of expression in mature erythrocytes might be due to the long life of these cells after enucleation, during which time the βgeo protein is degraded.

Because of the ubiquitous expression of βgal, ROSA 26 mice should be useful to monitor engraftment of transplanted hematolymphoid cells, whether they are primitive stem/progenitor cell populations or mature end-stage cells. To this end, several bone marrow transplantations into lethally-irradiated (750 rads) recipient C57BL/6J mice were performed, using either whole BM (2×10$^6$) or cells partially-enriched for hematopoietic stem/progenitor activity by sorting for cells which do not express antigens present on lineage-committed hematopoietic cells (1×10$^5$ Lin$^-$). These cells were isolated from heterozygous ROSA26 mice backcrossed three generations to C57BL/6J and sorted to be CD5$^-$Mac1$^-$B220$^-$CD4$^-$CD8$^-$Gr-1 (Lin$^-$). βgal expression in the hematolymphoid compartment of these mice showed that, 4 weeks after transplantation, bone marrow-derived progenitor cells could reconstitute all major hematolymphoid lineages as evidenced by the high proportion of βgal$^+$ cells found in nucleated cells of bone marrow (BM), spleen (Spl) and thymus (Thy). FACS-Gal analysis done in combination with antibody stains to delineate the various lineages showed that while there had been nearly complete donor cell reconstitution of B-lineage cells (B220$^+$) and myeloid lineage cells (Mac1$^+$) in the periphery, there had not yet been significant contribution of donor-derived progenitor cells to the peripheral T cell compartment (high CD5+) as evidenced by the overwhelming proportion of βgal$^-$ (host origin) T cells (high CD5$^+$) in the spleen of mice reconstituted with either whole bone marrow (WBM) or Lin$^-$ cells.

The majority of mature T cells (high CD5$^+$) in the spleens of all the reconstituted mice 4 weeks after transplantation were βgal$^-$ and therefore of host origin (C57Bl/6J). To test whether thymic progenitor cells of host origin were giving rise tb these peripheral T cells, the major developmental stages of T lymphopoiesis were analyzed for βgal expression as a marker of donor vs. host origin. This analysis showed that in the animals reconstituted with whole BM, nearly all cells present in the major stages of T-lymphopoiesis (CD4$^-$8$^-$, CD4$^+$8$^+$, CD4$^+$8$^-$, CD8$^+$4$^-$) were βgal$^+$ and therefore of donor origin suggesting that the host-derived T cells might be derived from long-lived, radioresistant T cells. However in thymocytes of the animal reconstituted with Lin$^-$ BM cells (Lin$^-$ Thymus), while the overwhelming majority of he more immature T cell progenitor populations (CD4$^+$8$^+$, D4$^-$8$^-$) are βgal$^+$ and therefore of donor origin, there was still significant host contribution to single positive (CD4$^+$8, CD8$^+$4$^-$) thymocytes. This suggests that peripheral T cells of host origin could be derived from residual thymic progenitors as well as radioresistant mature T cells. The successful engraftment of lethally-irradiated animals by βgal$^+$ ROSA26-derived BM progenitor cells as monitored by multiparameter FACS-Gal analysis confirming the utility of the ROSA26 strain for studies of bone marrow transplantation and delineation of the developmental potential of stem/progenitor cell populations.

The ROSA26 Region Produces Three Transcripts.

5' RACE was employed to identify exons from the trapped gene. The RACE product contained 130 bp of unique sequence. To confirm that this sequence was derived from the trapped gene, it was used as a probe on Southern blots of StuI digested DNA from wild type, heterozygous and homozygous ROSA26 mice. The probe identified an RFLP (wildtype band of approximately 7 kb and mutant band of approximately 12 kb) that co-segregates with the ROSA26 allele.

The unique sequence was used to design primers for 3' RACE. Two classes of products were obtained. Both contained identical 5' ends but diverged at their 3' ends. These 3' RACE products were used as probes on cDNA libraries. Multiple cDNAs were obtained for one of the two RACE products and their sequence was used to piece together an 1,170 nucleotide (nt) cDNA referred to as transcript 1 (Table 2; SEQ ID NO: 7), that contains a poly A addition signal 20 nucleotide 5' of its 3' poly A tail. The second 3' RACE product was used as a probe on several cDNA libraries but only one 412 nucleotide cDNA, referred to as transcript 2, was obtained (Table 3; SEQ ID NO: 8). Further 3' RACE identified transcript 2 messages as long as 2.1 kb. Searches of both transcripts 1 and 2 revealed no significant open reading frames (ORFS) nor any similarities to known sequences.

While probing cDNA libraries for transcript 2, multiple cDNAs were obtained with identity to transcript 2 sequences, but transcribed from the complementary strand. Sequencing of these cDNAs identified a 2 kb cDNA. This cDNA, referred to as transcript AS (anti-sense) (Table 4; SEQ ID NO: 9), contains an ORF of at least 1605 nucleotides that begins at the 5' end. The cDNA sequence contains a poly A addition signal 25 nt from the 3' poly A tail. 5' RACE was used to find additional 5' sequence, but identified the same 5' end suggesting the cDNA may be full length. The most 5' in-frame ATG codon is in the context of a Kozak (Kozak, M., J. Cell. Biol. 108:229–241 (1989)) start site and may encode the translation initiation site. Searches of the database with an amino acid sequence deduced from the open reading frame (ORF) (Table 5; SEQ ID NO: 10) identified one gene cloned by the C. elegans genome project with an overall similarity of 59.5% and identity of 40.5%. In addition, three human expressed sequence tags (ESTs) were found that had sequence identities with transcript AS ranging from 77 to 86%. Transcript AS contains no overlap with transcript 1, but overlaps with transcript 2 over 381 nucleotides all contained within transcript AS coding sequence. Thus the ROSA26 region encodes three transcripts, two noncoding and one coding transcript that is highly conserved in evolution.

Loss of the Noncoding Transcripts in ROSA26 Homozygotes.

To determine the effect of the retroviral integration on the expression of the 3 transcripts, Northern blot and RT-PCR studies were carried out. Transcript 1 was present in all wild type tissues, but absent in all mutant tissues. By contrast, reprobing the same Northern revealed that transcript AS is present in all tissues of both wild type and mutant mice and confirmed the integrity of RNA. The approximately 1.4 and 2.0 kb sizes of transcripts 1 and AS, respectively, suggest that the cDNAs isolated must be nearly full length. Probing of polysomal RNA showed that transcript AS was present on polysomes while transcript 1 was not. Furthermore, in vitro translation of transcript 1 failed to produce a protein product.

RT-PCR was carried out on kidney RNA from wild type and ROSA26 mutant mice to examine the effects of retroviral integration on expression of transcript 2, as it could not be detected by Northern blots. This analysis confirmed the previous results on expression of. transcript 1 and AS, and showed that transcript 2 expression was eliminated in mutant mice.

Mapping of the ROSA26 Genomic Region.

A transcript 1 probe was used to screen a 129Sv genomic library to clone the ROSA26 genomic region. PCR was used to amplify the ROSA26 mutant genomic DNA. The wild type ROSA26 genomic region was mapped and transcripts 1, 2, and AS exon sequences and the ROSAβgeo integration site were identified. The ROSAβgeo provirus has integrated into the first intron of transcript 1 and 2 with the splice acceptor sequence oriented. in a position to trap both transcript 1 and 2. Transcript 1 and 2 share exon 1 and the 5' end of the second exon,. but transcript 1 continues to be transcribed. through the genomic DNA while transcript 2 splices to a third exon. This third exon of transcript 2 overlaps with the final exon of transcript AS resulting in a sense-antisense relationship between these transcripts. Transcript AS is in reverse orientation to transcripts 1 and 2 and thus cannot be trapped by the SA sequence of ROSAβgeo.

Backcross panel mapping was used to identify the chromosomal location of ROSA26. Southern blots of mouse genomic DNA were used to identify a MspI RFLP between Mus musculus and Mus spretus DNA. Backcross panel DNAs were obtained from the Jackson Labs and MspI blots were probed to demonstrate that the ROSA26 region maps to mouse chromosome 6 with no crossovers with the marker D6Mit10.

Rosa 26 Transcript Promoter Identified.

Because ROSA26 may be a useful region for targeting ubiquitous expression of various genes, sequences 5' of exon 1 of transcripts 1 and 2 were tested for promoter activity. Primer extension was used to identify three transcription start sites (see Genbank accession # U83173) and GC and CAAT boxes, but this region lacks a TATAA sequence. These features are common for housekeeping gene promoters. To identify the promoter, various fragments were fused to a βgal reporter gene. A potential translation start site within exon 1 was mutated to a BamHI site, as it might prevent proper translation of βgal. A wild type fragment containing the potential translation start site was also fused to βgal as was the PGK promoter as a positive control and no promoter as a negative control. All constructs also contained a PGK promoter directing the expression of the neomycin resistance gene for positive selection. Constructs were electroporated into ES cells and following G418 selection, βgalactosidase activity was determined on extracts from pooled colonies. The PGK promoter produced the highest βgal activity and the promoterless construct and mock electroporated ES cells produced almost no βgal activity. All ROSA26 promoter fragments tested had promoter activity in ES cells albeit at lower levels than observed with the PGK promoter. This might be due to position effects on integration of the transgene, as ES cells isolated from ROSA26 mice were found to have 3 fold more βgal activity than was observed with the PGK promoter. Removal of the potential translation start site improved the expression of βgal. Moreover, the 1 kb promoter containing fragment has been found to direct high level, widespread expression of a reporter gene in transgenic mice.

EXAMPLE II

In this example a general deletor vector has been constructed to insert a gene encoding a heterologous recombinase into a ubiquitously expressed gene locus. This construct was used to transform mice to form a general deletor mouse strain. The specific general deletor mouse formed in this example has the Cre recombinase operatively associated and under the control of the ROSA26 promoter gene locus. The general deletor mice exploit the ability of the Cre recombinase to specifically delete sequences flanked by lox sites in the same orientation. This provides for a general deletor mouse that when crossed with various mutant mice containing sequences flanked by lox sites (e.g., those made for making conditional mutations in the mouse), deletes the flanked sequence in the germ line.

Figure 1A:
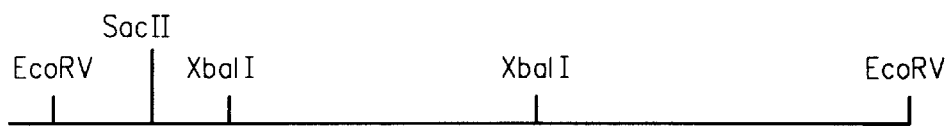
FIGS. 1A–1D provides maps of the ROSA26 gene locus and the design of representative General Deletor and General Reporter target vectors.

A ROSA26 genomic clone was isolated from a genomic library prepared from 129/Sv mice (Soriano et al., Cell 64: 693–707 (1991); which is incorporated by reference herein) using a $^{32}$P-radiolabeled probe to the ROSA26 transcript 1. Plasmid pPGKneolox2DTA (Soriano, Development 124: 2691–2700 (1997); which is incorporated by reference herein) containing the Diphtheria toxin gene (DTA, a negative selection marker) under the control of the PGK promoter provided the vector backbone for the targeting construct. A 5 kb Sac II-Xba I fragment comprising the genomic 5' untranslated sequence of ROSA26 and containing a unique intronic Xba I site was inserted between the Nhe I and Sac II sites of the pPGKneolox2DTA vector such that the. ROSA26 fragment was inserted upstream of the PGK promoter-DTA expression cassette (FIG. 1A). The unique Xba I site is close to the normal site of insertion of the original ROSAβgeo provirus. Following insertion of various reporter constructs and a selectable marker (e.g. neo) at the Xba I sites, this targeting vector results in targeting events in 30%–50% of G418$^r$ colonies.

Figure 1B:
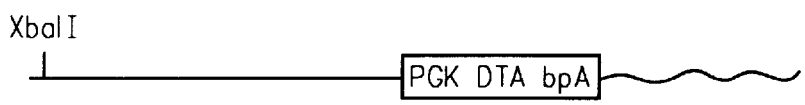

To construct the general deletor targeting vector, a Spe I-Sal I fragment containing an Adenovirus splice acceptor (SA) joined to a sequence encoding the bacteriophage P1 Cre recombinase (Sauer and Henderson, Proc. Natl. Acad. Sci. USA 85:5166–5170 (1988)) and a Sal I-Xba I fragment containing a PGK promoter-neo gene are inserted into the unique Xba I site of the general targeting construct (FIG. 1B). A general deletor construct containing the Cre insert in the proper orientation relative to the ROSA26 promoter sequence is selected.

The targeting construct was linearized and transfected by electroporation into mouse embryonic stem (ES) cells. A 129/Sv derived ES cell line, AK-7, described by Zhuang et al. (Cell 79:875–884 (1994); which is incorporated herein by reference in its entirety) was used for electroporation. These ES cells were routinely cultured on mitomycin C-treated (Sigma) SNL 76/7 STO cells (feeder cells) as described by McMahon and Bradley (Cell 62: 1073–1085 (1990); which is incorporated herein by reference in its entirety) in culture medium containing high glucose DMEM supplemented with 15% fetal bovine serum (Hyclone) and 0.1 mM β-mercaptoethanol.

To prepare the targeting construct for transfection, 20 μg of the targeting construct was linearized by digestion with Sac II, phenol-chloroform extracted, and ethanol precipitated. The linearized vector was then electroporated into $10^7$ ES cells. The electroporated cells were seeded onto two gelatinized plates with a subconfluent layer of mitomycin-C inactivated SNL 76/7 STO feeder cells and cells containing the targeting vector were selected in the presence of G418. The culture medium for each plate was changed every day for the first few days, and then changed as needed after selection had occurred. Colonies of ES cells with true homologous recombination (HR) events, in which the general deletor construct was inserted into the ROSA26 gene were identified by PCR. After 10 days of selection, a portion of each colony was picked microscopically with a drawn micropipette, and was directly analyzed by PCR as described by Joyner et al. (Nature 338:153–156 (1989); which is incorporated herein by reference in its entirety). Briefly, PCR amplification was performed as described (Kogan et al., New England J. Med. 317:985–990 (1987); which is incorporated herein by reference in its entirety) using 4 cycles of 93° C. for 30 seconds, 36 cycles of 93° C. for 30 seconds, 55° C. for 30 seconds, and 65° C. for 2 minutes using primers cct aaa gaa gag gct gtg ctt tgg (SEQ ID NO: 17) and cat caa gga aac cct gga cta ctg (SEQ ID NO: 18) from the ROSA26 promoter and the splice acceptor sequence (in reverse orientation), respectively. Positive colonies, identified by PCR, were subcloned into 4-well plates, expanded into 60 mm plates and frozen into 2–3 ampules. Southern blot analysis using probes external to both the 5' and 3' end of the targeting construct confirmed that a true homologous recombination event had occurred in each of eight clones surveyed.

To generate chimeric mice, eight positive clones were trypsinized into single cells, and blastocysts obtained from C57BL/6J mice were each injected with approximately 15 cells from an individual clone. The injected blastocysts were then implanted into pseudopregnant F1 mice (C57BL/6J× 129/Sv). Chimeric pups with predominantly agouti coats (indicating a major contribution of the ES cells to the somatic tissues) were selected for further breeding. Three chimeras, subsequently identified representing two separate ES cell clones, were bred to C57BL/6J females. The chimeric males were also bred to 129/Sv females to place the mutation in a congenic background. Once germline transmission had been observed, as determined by PCR analysis of resulting offspring, chimeras are 129Sv mice to homogeneity to maintain the lines on an inbred background. The chimeras-were also back crossed to homogeneity onto a C57BL6/J background.

The general deletor mice were crossed with mice that contain a conditional allele at the PDGFαR locus in which various exons of the gene are flanked with lox sites in the same orientation. Recombination at this locus in the resulting offspring has been verified by Southern blot analysis. The mice are crossed to the reporter mice described below to test for ubiquitous expression of β-galactosidase.

EXAMPLE III

In this example a general reporter vector is constructed wherein a βgalactosidase gene is introduced downstream of a neo gene under the control of a PGK promoter and upstream of four polyadenylation sites. The neo gene is flanked by two lox sites which are recognition sites for Cre recombinase. The reporter mice exploit the ability of the Cre recombinase to specifically delete sequences flanked by lox sites. In this embodiment the ROSA26 promoter is engineered to express a detectable marker only following expression of Cre recombinase, as its expression is otherwise prevented by a stuffer fragment flanked with lox sites. To facilitate the screening for homologous recombination at the ROSA26 locus, the stuffer fragment contains a selectable neo expression cassette.

Figure 1C:
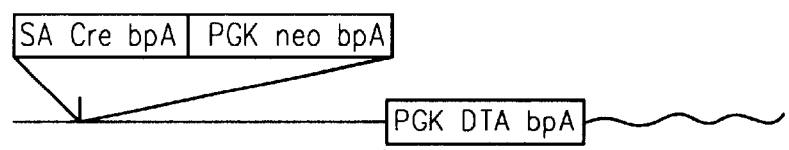
Figure 1D:
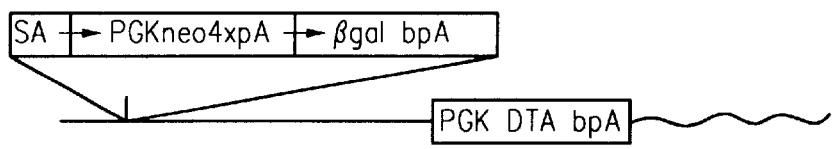

Reporter mice are generated by first constructing a reporter target construct (FIG. 1C), based on the general target construct discussed above (FIG. 1A). To construct the reporter target construct, an Xba I fragment comprising the Adenovirus splice acceptor joined to a neo expression cassette under the control of the PGK promoter followed by four polyadenylation sequences to prevent read-through, flanked by lox sites in the same orientation, joined to the approximately 3.1 kb sequence encoding the βGal gene and followed by a bovine growth hormone polyadenylation site, is inserted into the unique Xba I site of the general targeting construct (FIG. 1C). A reporter target construct containing the insert in the proper orientation relative to the ROSA26 promoter sequence is selected.

The targeting construct was linearized with Kpn I and transfected by electroporation as described above. Colonies of embryonic stem (ES) cells with true homologous recombination (HR) events, in which the reporter construct was inserted into the ROSA26 gene were identified by PCR using the same oligonucleotides as described above for the general deletor strain. Positive colonies, identified by PCR, were subcloned into 4-well plates, expanded into 60 mm plates and frozen into 2–3 ampules. Southern blot analysis using probes external to both the 5' and 3' end of the targeting construct confirmed that a true homologous recombination event had occurred in each of eight clones surveyed.

To generate chimeric mice, five positive clones were trypsinized into single cells, and blastocysts obtained from C57BL/6J mice were each injected with approximately 15 cells from an individual clone. The injected blastocysts were then implanted into pseudopregnant F1 mice (C57BL/6J× 129/Sv). Chimeric pups with predominantly agouti coats (indicating a major contribution of the ES cells to the somatic tissues) were selected for further breeding. Five chimeras, subsequently identified representing three separate ES cell clones, have transmitted the mutant allele through the germ line as judged by PCR analysis and the resulting offspring will bred to C57BL/6J females. The chimeric males are bred to 129/Sv females to place the mutation in a congenic background and to maintain the lines on an inbred background. The chimeras are also back crossed to homogeneity onto a C57BL6/J background.

When the general reporter mice are crossed with the general deletor mice as described above in Example II the neo gene will be excised by the Cre recombinase. As the Cre gene is under control of the ubiquitous promoter ROSA26 the excision of the neo gene would be expected to take place in essentially all cells of the descendant mice.

EXAMPLE IV

In this example the gene carrying the retroviral promoter trap in the cell line BT-5 was identified and modified for use as a general reporter (universal conditional reporter (UCR)) locus. BT-5 animals carry a single-copy insertion of the ROSA β-Geo promoter trap sequence which confers ubiquitous expression of β-galactosidase throughout embryogenesis. The insertion was identified to occur in a gene designated G3BP. Modification was accomplished by inserting a loxP flanked drug selection cassette into the lacZ coding sequence.

Further, a recombinase expressing allele was introduced into a conditionally expressed endogenous gene by homologous recombination. Also, rather than inserting the recombinase coding sequence in frame within the endogenous locus, an Internal Ribosomal Entry Site (IRES)-Cre recombinase cassette was constructed to increase the efficiency of Cre expression. The IRES-Cre cassette was inserted under the control of the conditional endogenous regulatory elements of the EphA2 gene for expression. Embryos heterozygous for both the Cre and UCR alleles were generated which demonstrated that Cre recombinase was efficiently expressed in vivo from the IRES allele, and that the UCR locus was restored in EphA2-expressing cells from early stages of embryogenesis onward.

Materials and Methods
Rapid Amplification of cDNA Ends Total RNA was isolated from the SM3 BT5/+ ES-cell line using Trizol (Gibco BRL) and 5'Rapid amplification of cDNA ends (RACE) was essentially performed as previously described (Townley et al., *Genome Research* 7:293–298 (1997)). First strand cDNA was synthesized from 5 µg of total RNA using primer 1, 5'-taatgggataggttacg-3'; (SEQ ID NO: 19). After tailing, second strand synthesis was performed using primer 2, 5'-ggttgtgagctcttctagatgg(t)$_{17}$-3'; (SEQ ID NO: 20) and products were subjected to 30 cycles of PCR amplification using adapter-primer 2, 5'-ggttgtgagctct tctagatgg-3'; (SEQ ID NO: 21) and a primer specific to the ROSA βgeo vector, 5'-agtatcggcctcaggaagatcg-3'; (SEQ ID NO:

22). A second round of PCR was performed using adapter-primer 2 and a further nested vector primer, 5'-attcaggctgcgcaac tgttgg-3'; (SEQ ID NO: 23). Amplified products were cloned into plasmid pGEMT (Promega) and sequenced. The BLAST algorithm (Altschul et al., *J. Mol. Bio.* 215:403–410 (1990)) was used to search the GenBank databases for sequence homologies.
Derivation of Mutant Mice A genomic library was prepared by partial Sau3A digestion of BT-5/+ 129SvEv DNA followed by size fractionation in a 0.8% agarose gel (FMC Seachem-Gold) and electroelution of restriction fragments in the 9–23 kb size range. Recovered DNA was ligated into BamHI digested λ-Dash bacteriophage arms (Stratagene) and subsequently packaged using GIGAPACK GOLD packaging extracts as described by the manufacturer (Stratagene). This library was screened using probes from the 5' and 3' ends of SAβGeo to isolate clones spanning the retroviral insertion, followed by restriction mapping using T3/T7 oligomer hybridization.

The BT-5 targeting vector was prepared by using in vitro mutagenesis (Promega kit) to create an NcoI site at the start codon of SAβGeo (gac atg to gcc atg). A double stranded loxP oligomer (5'-catggcc agatctagaataacttcgtatagcatacattatac gaagttatca-3'; (SEQ ID NO: 24) with cohesive NcoI and HindIII termini was cloned between the mutagenized NcoI of SAβGeo and the HindIII site of pFRT-βGal (O'Gorman et al., *Science* 251: 1351–1355 (1991)). Sequence from the HindIII site to the EcoRV site of pFRT-βGal replaces the corresponding region of SAβGeo in the targeting vectors. The PGK-Hygro cassette, (Mortensen, et al., *Proc. Natl. Acad. Sci. USA* 88:7036–7040 (1991), was cloned in as a BamHI-HindIII (5'-3') restriction fragment in reverse orientation to become loxP flanked using the oligomer sequence as follows; NcoI-5' LoxP-HindIII-reversed hygro cassette-(BamHI/BglII fusion)-3, LoxP-HindIII-pFRT-βGal. The BglII site used is underlined in the oligomer above; this removes the start codon from the downstream loxP oligomer. The sequence which remained following Cre mediated excision of the cassette is the sequence of the oligomer described above. The NotI-XhoI restriction fragment was cloned into the corresponding 5' sites in SAβGeo to provide 5' homology. The XhoI fragment was ligated into the SalI site at the 3' end of βGeo to provide 3' homology. All vectors were prepared for transfection using cesium chloride equilibrium density centrifugation and linearization with NotI.

To target the endogenous EphA2 locus, a fragment of the EphA2 cDNA (Ruiz and Robertson, *Mech. Dev.* 46:87–100 (1994)) was used to screen a 129/SvJ genomic library (Stratagene). A phage clone containing an exon for nucleotides 1076 to 1395 within the extracellular domain was selected for detailed characterization to prepare a targeting vector incorporating the IRES cassettes. (FIG. 5A). Flanking homology on the 5' side is provided by a 2.8 kb SacI-HindIII restriction fragment while 3' homology is provided by a 6.2 kb EcoRI restriction fragment. All vectors were prepared as described above and were linearized with XhoI prior to transfection.

SM3 (BT5/+) or CCE ES cells (2×10$^7$ per 0.5 ml), maintained on STO-neo-Hygro feeder cells, were electroporated (200v, 960 µF; Biorad gene pulser) with 15 µg linear targeting vector. Following low density plating (4×10 cm plates) and recovery for 36 hours, cells were selected in either G418 (200 µg/ml) or hygromycin (100 µg/ml) (Robertson et al., *Nature* 323:445–448 (1986); Poirier and Robertson, *Development* 119:1229–1236 (1993)). Drug resistant colonies were individually transferred into 96 well microtiter plates and expanded. Replica plates were screened by Southern blot analysis as previously described (Ramirez-Solis et al., *Methods Enzymol.* 22:855–877 (1993)).

Hygromycin resistant clones resulting from transfection of CCE ES cells with the BT-5 targeting vector were examined by Southern Blot. Briefly, genomic DNA was digested with SacI and hybridized with probe I. The presence of a 9.0 kb fragment was indicative of a fragment derived from the wild-type locus and a 7.5 kb fragment was indicative of a fragment derived from the targeted locus. Targeted cell lines were tested for conditional reporter activation by using a representative targeted Universal Cell Reporter (UCR) ES cell line which had been mock-transfected and a cell line transfected with 20 µg pMC13-Cre, partially selected in G418 (200 µg/ml) and then stained for LacZ activity. Cre transfection restores lacZ activity and resistance to G418. Duplicate plates from this experiment were subjected to Southern blot analysis to confirm the expected DNA rearrangement. DNA from two such experiments was digested with NcoI and hybridized to probe II. (See FIG. 3C). A 3.5 kb fragment resulted from excision of the Hygro cassette and 5.5 kb fragment from the unrearranged locus. A small hybridizing fragment was expected to develop in each experiment and was the result of the probe spanning the NcoI site.

To confirm insertion of the various IRES-Cre cassettes Southern blot analysis of G418 resistant clones resulting from transfection of CCE ES cells were carried out. Genomic DNA from each clone was digested with BglII and XbaI and hybridized with probe III. The presence of a 7.0 kb fragment is indicative of a fragment derived from the wildtype allele and presence of a 4.4 kb fragment is indicative of a fragment derived from the modified allele.

Correctly targeted clones for chimera analysis or germline transmission were microinjected into C57Bl/6J host blastocysts and transferred to pseudopregnant MF1 foster mothers using standard procedures (Bradley, in E. J. Robertson (Ed.), Teratocarciromas and embryonic stem cells; a practical approach, pp. 131–151., IRL Press, Oxford, UK (1987)). Germline transmission and genotype was determined using the same Southern blot analysis used to identify targeting events described above.

Preparation and testing of IRES-Cre cassettes IRES-Cre2, subsequently used in all targeting vectors, was prepared by blunt end ligation of the HindIII site 3' to the IRES in IRES-βGeo (Mountford et al., *Proc. Natl. Acad. Sci. USA* 91:4303–4307 (1994)) to the XbaI site at position –9 from the start codon of the Cre coding sequence in pMC13-Cre (Gu et al., *Cell* 73:1155–1164 (1993)). Each cassette was cloned into PGK-Neo IRES-LacZ (Mountford et al., *Proc. Natl. Acad. Sci. USA* 91: 4303–4307 (1994)) to replace the IRES-LacZ component. Twenty micrograms of each supercoiled plasmid was electroporated into conditional reporter ES cells and, 48 hours later, selection initiated in G418 (200 μg/ml). LacZ expression was assessed 3–5 days later by fixing in 0.5% glutaraldehyde in PBS for 5–10 minutes, washing 3 times in PBS and incubating in X-gal reagent described below but omitting NP-40 and deoxycholate. This protocol was used for staining all ES cells in this study.

Embryo Analysis Animals were sacrificed by halothane inhalation. Embryos were dissected free of maternal tissues, the Reichert's membrane reflected and fixed 30 to 90 minutes in 0.5% glutaraldehyde, 1% formaldehyde, 2 mM $MgCl_2$, 5 mM EGTA in PBS at 4 degrees. Embryos were washed 3 times in PBS, 0.02% NP40 and incubated 12–48 hours at 37° C. in X-gal reagent (5 mm each of potassium ferricyanate and potassium ferrocyanate, 2 mM $MgCl_2$, 0.02% NP40, 0.01% deoxycholate and 0.5–1.0 mg/ml X-gal in PBS). Embryos were washed in PBS and post-fixed in 0.5% glutaraldehyde, 1% formaldehyde in PBS, and photographed in 80% glycerol. For histology, embryos were dehydrated in a graded ethanol series, cleared in xylenes and embedded in paraffin wax. Eight μm sections were dewaxed in xylenes, mounted in cytoseal and photographed using Nomarski optics.

Results
Preparation of the Universal Conditional Reporter Mouse Line

Figure 2:
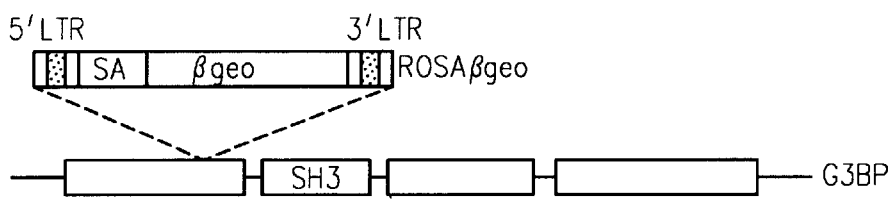
FIG. 2 depicts a schematic of the G3BP gene showing the retroviral promoter trap insertion site and a schematic of the cassette comprising the ROSA βgeo retrovira[008c] insert. Shaded areas represent structural motifs associated with RNA binding proteins. SA, splice acceptor; LTR, long terminal repeat; SH, SH3 domain binding sequence.

The BT-5 mouse line was generated by infection of ES cells with the ROSA β-geo retroviral promoter trap vector (Friedrich and Soriano, *Genes Dev.* 5:1513–1523 (1991), incorporated herein by reference in its entirety) and as described above. The gene disrupted in the BT-5 line was identified by cloning sequences flanking the insertion site using 5' RACE. The insertion occurred in a gene designated G3BP which encodes a protein known to bind to the SH3 domain of the ras-GTPase-activating protein ($GAP^{120}$; Kennedy et al, *Biomed. Pept. Proteins Nucleic Acids* 2:93–99 (1996) and FIG. 2). Recent data suggests that G3BP can initiate mRNA degradation and therefore may represent a link between ras-GAP-mediated signaling pathways and RNA turnover (Gallouzi et al., *Mol. Cell. Biol.* 18:3956–65 (1998)). Intercrosses between BT-5 heterozygotes reveal that animals homozygous for the insertion are viable and fertile indicating that the activity of G3BP is not essential for normal development.

In agreement with transcript analysis of G3BP (Kennedy et al., (1996), supra), the βgal reporter in BT-5 mice was expressed in a strong and ubiquitous manner from gastrulation to organogenesis. Weak lacZ expression was noted in the primitive endoderm of the 7.5 d.p.c. embryo and in the loose mesenchyme ventral to the neural tube at 10.5 d.p.c. The appearance of expression of lacZ may be due in part to the low cell density in these tissues.

Figure 3A:
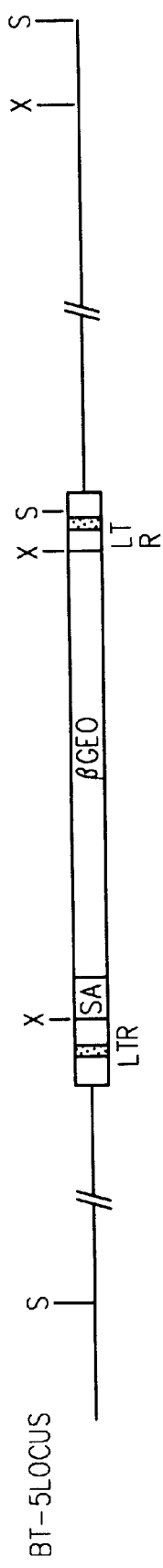
FIGS. 3A through 3D depict the method used to derive the conditional reporter lacZ allele at the site of the BT-5 retroviral insertion.

A bacteriophage genomic library was prepared from BT-5/+ DNA and screened using retroviral sequence as a probe to isolate restriction fragments. spanning the retroviral insertion. A 3.5 kb NotI-XhoI fragment and 6.5 kb XhoI fragment contain the host gene-retroviral LTR upstream and downstream junction fragments, respectively, and were used to prepare the targeting vector (FIG. 3A). Homologous recombination of this targeting vector into the corresponding wildtype locus in CCE ES cells recreates all aspects of the original BT-5 retroviral insertion except that the β-Geo coding sequence was interrupted, and therefore inactivated, by insertion of a loxP-flanked PGK-Hygromycin resistance gene cassette (PGK-Hygro) at its 5' end (Mortensen et al., (1991), supra). The PGK-Hygro cassette lies in reverse transcriptional orientation relative to the lacZ coding sequence to prevent inadvertent transcription of β-Geo from the PGK promoter. (FIG. 3B and FIG. 3C) LacZ activity was restored by a Cre-mediated rearrangement to remove the PGK-Hygro cassette, leaving a loxP site immediately downstream from the β-Geo start codon. The position of the loxP sites must therefore preserve the β-Geo reading frame once excision of the PGK-Hygro cassette has occurred. (FIG. 3D).

Figure 3B:
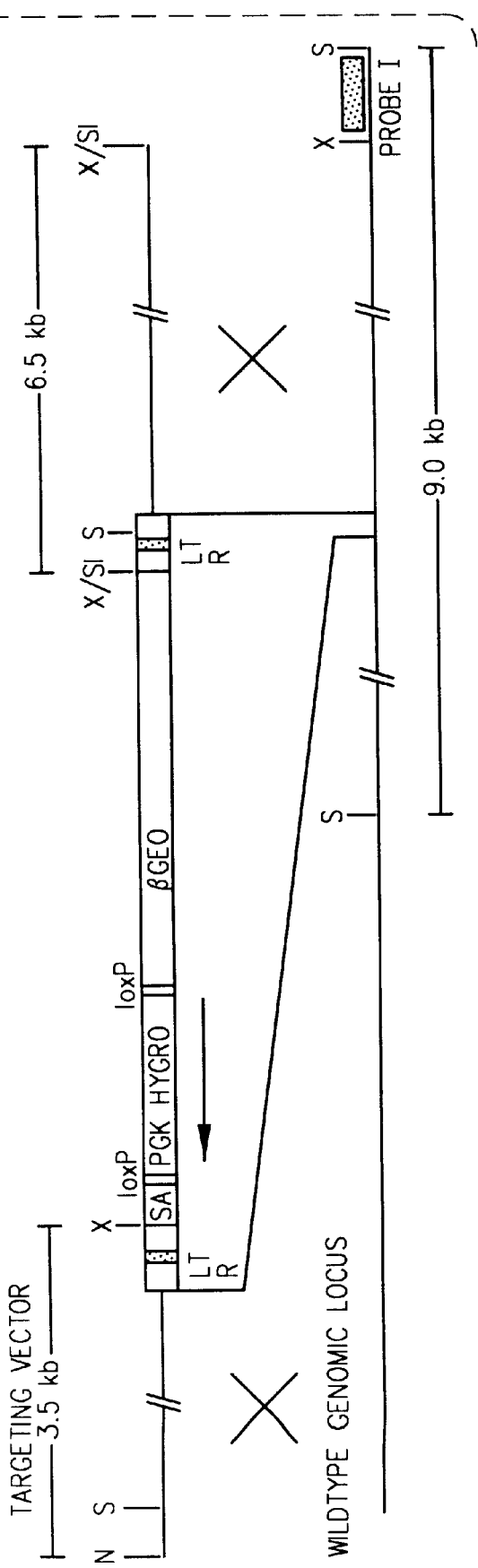
Figure 3C:
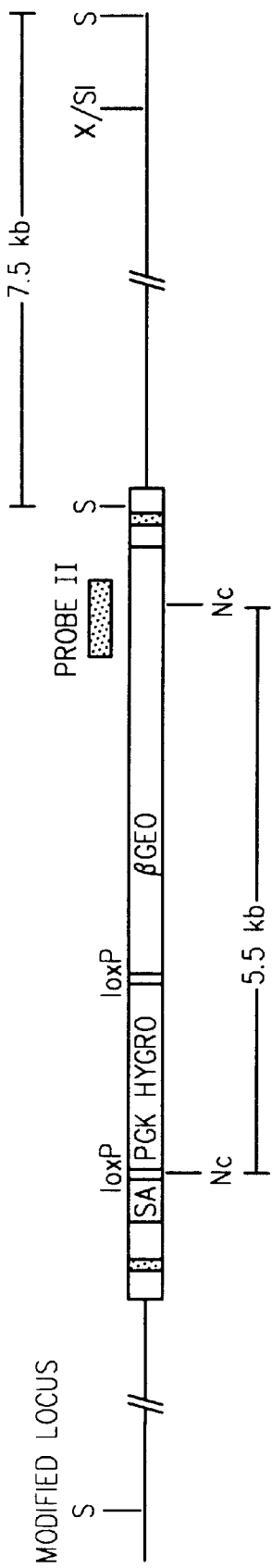
Figure 3D:
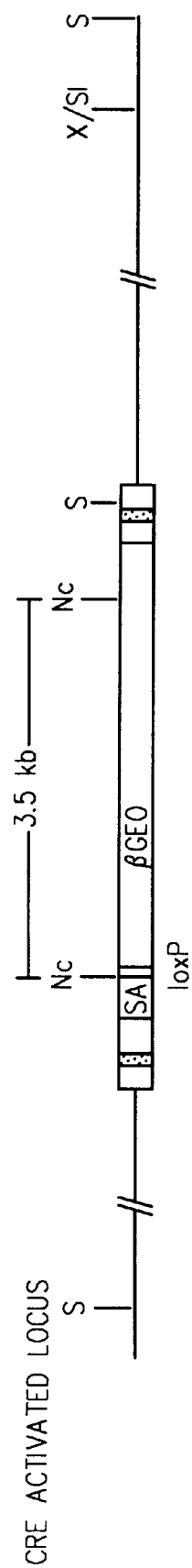

Hygromycin-resistant clones resulting from transfection of CCE ES cells with the targeting vector were screened by Southern blot hybridization using an external probe to identify a SacI polymorphism (FIG. 3B). Analysis of 300 clones revealed 22 targeting events. To determine if β-galactosidase activity can be restored in the targeted cell lines, twelve clones were individually expanded and transfected with the Cre expression plasmid, pMC13-Cre (Gu et al., *Cell* 73:1155–1164 (1993)) followed by partial selection in G418. Control cultures of mock-transfected cells were clearly dying in the presence of G418 and failed to express β-galactosidase. Eight of the pMC13-Cre transfected cell lines, in contrast, were surviving in G418 and strongly expressed β-galactosidase, indicating that the activity of β-Geo has been efficiently restored by Cre recombinase in vitro. This result was verified by Southern blot analysis using an NcoI digest to detect the Cre recombinase-mediated excision event. In ES cells, β-Geo expression from the unrearranged conditional reporter locus is completely abolished, failing even to permit survival of cells in G418. Activation by Cre recombinase, however, leads to robust expression of lacZ, indicating that the remaining loxP site does not detectably diminish expression levels of β-Geo in vitro.

Three targeted cell lines (CBT-B2: CBT-B4: CBT-C5) were used to generate germ line chimeras, allowing the establishment of three separately derived conditional reporter mouse lines. One line (CBT-B2) was used in all subsequent experiments described below and is referred to as the universal conditional reporter (UCR1) mouse line.

Southern blot analysis from this targeting experiment consistently revealed a nonmolar, less intense signal corresponding to the targeted allele as compared to the wildtype allele, suggesting that the copy number of the host gene in which the BT-5 retroviral insertion resides may be greater than one per haploid genome. To further examine this possibility, 26 progeny obtained from a BT-5 heterozygous intercross were genotyped by the same Southern blot analysis. Three animals carried only the wildtype allele. The remainder carried both wildtype and BT-5 promoter trap alleles; 5 of these had equally intense hybridizing bands while the other 18 had notably more intense wildtype signals. Test breeding experiments confirmed that animals with equivalent molar ratios were indeed homozygous for the BT-5 retroviral insertion. Collectively, these data indicate that the copy number of the trapped locus is two per haploid genome. This finding may well explain the viability of BT-5 homozygotes. Extensive efforts to identify a restriction fragment length polymorphism to distinguish duplicated genes were unsuccessful.

An IRES-Cre Cassette Efficiently Expresses Cre Recombinase

The IRES sequence used in this example were derived from the Encephalomyocarditis virus (EMCV) (Jang et al., *J. Virol.* 62:2636–2643 (1988), Jang et al., *J. Virol.* 63:1651–1660 (1989); Jang and Wimmer, *Genes Dev.* 4:1560–1572 (1990); Ghattas et al., *Mol. Cell. Biol.* 11:5848–5859 (1991); and Mountford et al., *Proc. Natl. Acad. Sci. USA* 91:4303–4307 (1994)). The translational efficiency of a coding sequence linked to an IRES element is-sensitive to the spacing between the 3' end of the IRES and the start codon (Pilipenko et al., *Cell* 68:119–131 (1992). Three IRES-Cre cassettes were tested which differed only in the spacing between the IRES element and Cre coding sequence to determine the most efficient arrangement (FIG. 4). IRES-Cre #1 contains an IRES-ATG junction identical in sequence and spacing to that found in the native EMCV virus. IRES-Cre #2 was made by fusion of convenient restriction sites to link the IRES and Cre sequence elements. Although this cassette has a Kozak consensus sequence, the start codon is considerably further from the IRES than is considered optimal. IRES-Cre #3 has a junction identical to that found in IRES-β-Geo (Mountford et al., (1994), supra) Each IRES-Cre cassette was incorporated into a PGK-Neo-IRES-Cre pA plasmid which expresses a dicistronic transcript. An ES cell line carrying the conditional reporter allele was then transiently transfected with each construct to test for IRES mediated Cre activation of the target locus. The IRES-Cre #2 cassette had both substantially more activity than the other two cassettes, and possessed a surprisingly high overall level of expression, approaching 30–40% of that observed with the strongly expressed plasmid, pMC13-Cre in this cell line. The IRES-Cre #2 cassette was used in all subsequent experiments and is referred to simply as IRES-Cre.

Initial mapping studies of the EphA2 gene indicated that the genomic locus spans several phage clones and was therefore large. One phage clone characterized in detail contains a single exon corresponding to nucleotides 1076 to 1395 of the EphA2 cDNA, which is flanked by intron sequence on either side (FIG. 5A and FIG. 5B). A "positive-negative" targeting strategy was used previously to disrupt the EphA2 gene by inserting the PMC1Neo cassette into this exon. Since RES-driven cassettes require placement within exon sequence for expression, this targeting strategy was used to insert IRES cassettes into the EphA2 locus.

An IRES-β-Geo Allele of EphA2 Expresses LacZ in an EphA2-Specific Pattern

To confirm that an IRES sequence placed in this exon was both functional and expressed in a pattern faithful to EphA2-specific regulatory elements, a targeting vector containing IRES-β-Geo (Eph-IRES-Geo) was first prepared (FIG. 5A). From a single transfection experiment, a total of 23 G418 resistant clones were recovered, 19 of which were correctly targeted as detected by Southern blot analysis of genomic DNA from each clone digested with BglII and XbaI and hybridized with probe III (FIG. 5A). The high targeting efficiency (82%) reflects the "promoterless" nature of the targeting vector, random insertions of which rarely place the IRES cassette into transcriptionally active genomic locations necessary for its expression.

Expression of the IRES-Geo allele in vivo was assessed in chimeric embryos generated by microinjection of targeted cell lines into wildtype blastocysts. Robust lacZ expression in 9.0 and 10.0 day chimeric embryos was evident rostrally at the level of the otic vesicle and caudally in the tail of embryos examined for histology. The expression pattern of the Eph-IRES-β-Geo reporter allele at 9.0–10.0 dpc was in agreement with both RNA whole mount in situ hybridization experiments (Ruiz and Robertson, *Mech. Dev.* 46:87–100 (1994), incorporated herein by reference) and immunohistochemical staining using EphA2 specific antisera (Ganju et al., *Oncogene* 9:1613–24 (1994), incorporated herein by reference.) which demonstrate expression in the fourth rhombomere and adjacent structures, as well as the regressing caudal neuropore at the slightly earlier embryonic stages analyzed in this example. In addition, a LacZ gene trap retroviral insertion into the EphA2 gene (Chen et al., *Oncogene* 12:979–88 (1996), incorporated herein by reference) has a similar expression pattern at these stages, although the IRES-β-Geo targeted allele expresses lacZ much more robustly than the corresponding promoter trap insertion.

Whole mount views of lacZ stained embryos at 6.75 and 7.75 d.p.c. examined for histology demonstrated expression of Eph-IRES-β-Geo allele throughout the embryonic region at both stages. LacZ expression was present throughout the embryonic ectoderm but was clearly strongest on the posterior side in the area of the primitive streak. In the later stage 7.75 day embryo, anterior ectodermal expression diminished further but persisted in posterior ectoderm adjacent to the primitive streak. An anterior-posterior distinction was particularly evident in a less strongly chimeric embryo. In addition, lacZ expression was detected at this stage in newly formed mesoderm and definitive endoderm. Although RNA in situ hybridization experiments at these stages suggest a more localized distribution of transcript to the posterior side of the embryo (Ruiz and Robertson, (1994), supra), immunohistochemical analysis clearly revealed a substantially more widespread distribution of EphA2 protein to include anterior tissues (Chen et al., *Oncogene* 12:979–988 (1996), incorporated herein by reference) which is entirely consistent with the lacZ expression pattern of the IRES-β-Geo allele. The difference between RNA whole mount analysis and lacZ expression of the reporter allele is most likely explained by perdurance of lacZ protein and the increased sensitivity the latter technique frequently affords. A reporter allele for the nodal gene, for example, revealed posterior epiblast expression not previously evident on RNA whole mount analysis (Collignon et al., *Nature* 381:155–158 (1996)). Collectively, the results from this chimera analysis of the IRES-β-Geo reporter allele endorse previously characterized domains of EphA2 expression. The chimera experiments, however, suggested that expression of Cre protein from a corresponding IRES-Cre targeted allele might be more widespread in the early gastrulation stage embryo than previously suggested by RNA whole mount analysis. IRES-Cre is Functional in vitro When Inserted into the EpliA2 Locus The targeting vector was next adapted to introduce the IRES-Cre cassette into the EphA2 gene in CCE ES cells (FIG. 5A). A PGK-Hygromycin resistance gene flanked by FRT sites was linked to the 3' end of IRES-Cre (IRES-Cre-FRT-Hygro cassette) to provide a means of selection. The FRT sites allowed for subsequent removal of the PGK-Hygro component by FLP recombinase following targeting, if necessary. Two targeting vectors were prepared using flanking sequences exactly as described for Eph-IRES-Geo; the first construct incorporated the IRES-Cre cassette alone (Eph-IRES-Cre: FIG. 5A) and the second contained the IRES-Cre-FRT-Hygro cassette (Eph-IRES-Cre-FRT-Hygro: FIG. 5A).

To test if targeted alleles resulting from either vector were capable of expressing Cre recombinase, the targeting experiments were first performed in an ES cell line carrying the conditional reporter. locus. Following transfection, cultures were grown in G418 to identify clones in which Cre.-mediated activation of the conditional reporter locus had occurred. Since EphA2 is expressed in ES cells, targeting of this locus was expected to result in IRES mediated expression of Cre recombinase, followed by activation of the conditional reporter locus in some proportion of targeted cells.

Similar numbers of G418 resistant clones were identified for each vector while mock-transfected cultures yielded no clones. Southern blotting using probe III for integration demonstrated that 8 of 9 clones were correctly targeted at the EphA2 locus. These data indicate that the IRES-Cre cassette was functional to the same degree in both cassettes.

To obtain targeted cell lines capable of germline transmission, CCE ES cells were transfected with linearized Eph-IRES-Cre-FRT-Hygro targeting construct. Analysis of 288 Hygromycin resistant clones revealed 14 correctly targeted lines. One of these clones yielded chimeras capable of germline transmission and was used to establish the mouse line carrying the Eph-IRES-Cre-FRT-Hygro allele. This strain is subsequently referred to as the Eph-IRES-Cre mouse line.

Cell marking was demonstrated using embryos carrying both the conditional reporter- and Eph-IRES-Cre loci generated from an intercross of males heterozygous for the conditional reporter (UCR1) allele and females heterozygous for the Eph-IRES-Cre allele. Embryos recovered at 9.5 dpc. were analyzed for LacZ activity and genotyped by Southern blot hybridization of yolk sac DNA. A Hygromycin sequence probe was used to identify HindIII restriction fragments of 4.4 kb and 2 kb arising from the Eph-IRES-Cre and conditional reporter loci, respectively. Six of twelve embryos were double heterozygotes, and all contained cells expressing β-galactosidase. The remaining embryos had no detectable LacZ activity, including 2 embryos which carried the conditional reporter alone. This result demonstrates that the conditional reporter allele is functional in the context of the embryo, and that the unrearranged locus is completely silent in vivo until activated by Cre recombinase.

Representative LacZ stained double heterozygote embryos at 7.5, 8.5, 9.5, 10.5 and 12.5 dpc. were examined for β-galactosidase expression. Embryos at all stages examined contain a high proportion of cells which express β-galactosidase. Abundant lacZ expression was already evident throughout the embryonic region by 7.5 days, the earliest stage examined. Histological analysis demonstrated that in the embryonic region, cells of the ectoderm, mesoderm and definitive endoderm all contained an activated conditional reporter allele. In addition to embryonic region expression, there was abundant lacZ activity in the chorion consistent with the immunohistochemical staining pattern using EphA2 antiserum at gastrulation stages (Ganju et al., *Oncogene* 9:1613–24 (1994)). There was an absence of expression in this region of the Eph-IRES-Geo chimeras which was not unexpected since ES cells injected into blastocysts do not populate the chorion (Beddington and Robertson, *Development* 105:733–737 (1989)). Also, RNA whole mount analysis excluded extraembryonic components (Ruiz and Robertson, *Mech. Dev.* 46:87–100 (1994)). Extensive reporter activation by 7.5 dpc was entirely consistent with widespread expression of Cre recombinase predicted from the corresponding lacZ expression pattern of the Eph-IRES-β-Geo allele. However, the possibility that activation is also occurring in the pre-implantation embryo cannot be excluded (Chen et al, *Oncogene* 12:979–988 (1996)).

Embryos at 8.5, 9.5, 10.5 and 12.5 days were also extensively mosaic for lacZ(+) cells, as would be predicted from the conditional reporter activation observed by 7.5 dpc. An increased proportion of marked cells was evident in the caudal region of the embryo from 8.5 dpc onward and presumably reflects maintained expression of Cre recombinase in the node, notochordal and neural plates as these structures regress caudally. Also apparent at 10.5 dpc was a high proportion of lacZ(+) cells throughout the developing limb buds.

EphA2-receptor localizes to the distal mesenchyme as the limb buds elongate (Ganju et al., *Oncogene* 9:1613–1624 (1994): Gale et al., *Neuron* 17:9–19 (1996)). Histological analysis of the 9.5 day embryo revealed an area of more extensive conditional reporter activation superimposed on the mosaic pattern in the second branchial arch. Virtually all cells in the second branchial arch were lacZ(+), while the adjacent first arch (BA1) at this stage contained fewer lacZ(+) cells. Analysis of the hindbrain also revealed extensive reporter activation in the fourth rhombomere. In addition, a discrete cluster of cells adjacent to r4, rostral to the otic vesicle and in continuity with brachial arch 2, was also strongly lacZ(+). This structure is the early facio-acoustic (VII–VIII) cranial nerve nucleus. The cells marked in this cranial nerve nucleus and branchial arch 2 are neural crest in origin and have been shown to arise from the fourth rhombomere (for review see Lumsden et al., *Development* 113:1281–1291 (1991) and Kontges and Lumsden, *Development* 122:3229–3242 (1996), incorporated herein by reference). The pattern of conditional reporter activation in r4 was entirely consistent with the known expression of EphA2 in this segment (Ruiz and Robertson, (1994), supra). Although lacZ expression in neural crest cells most likely reflects conditional reporter activation in multipotential neural crest progenitors in r4 prior to their leaving the dorsal neural tube, the possibility also exists that activation was occurring in migrating crest cells, since expression of EphA2 is ongoing in branchial arch 2 as well as r4 (Ruiz and Robertson, (1994), supra). Extensive reporter activation was also consistently observed in adjacent branchial pouches and the rostral third branchial arch. Reporter activation in these regions may either represent mixing of r4 derived crest with cells from an adjacent rhombomeric compartment, or instead reflect a distinct r4 contribution to rostral brachial arch 3. On immunohistochemical analysis, the cells of rostral brachial arch 3 also clearly expressed EphA2 protein, suggesting a functional continuity with brachial arch 2 (Chen et al., (1996), supra). In the hindbrain, cells that have expressed the EphA2 receptor became highly spatially restricted to r4. In addition, neural-crest arising from this rhombomere segment were also clearly demarcated. Receptor expression thus appeared to commit cells to the r4 compartment.

Although the foregoing invention has been described in some detail by way of illustration and example for purposes of clarity of understanding, it will be obvious that certain changes and modifications may be practiced within the scope of the appended claims.

What is claimed is:

1. A method for making a genetically engineered non-human animal which ubiquitously expresses a heterologous DNA segment, the method comprising:

a) introducing into a pluripotent cell a DNA construct comprising a heterologous DNA segment and at least 100 base pairs homologous with a DNA sequence of an ubiquitously expressed endogenous gene locus of the pluripotent cell, where the DNA construct becomes integrated into the gene locus by homologous recombination, thereby inserting the heterologous DNA segment into the ubiquitously expressed endogenous gene locus such that expression of the heterologous gene segment is under the control of the promoter associated with the ubiquitously expressed endogenous gene;

b) selecting for pluripotent cells which carry the heterologous DNA segment under the control of the ubiquitously expressed endogenous gene locus promoter;

c) introducing the selected pluripotent cell into a developing non-human animal embryo;

d) allowing the developing embryo to develop to term; and e) identifying at least one offspring which carries the heterologous DNA segment integrated into the ubiquitously expressed endogenous gene locus under the control of the ubiquitously expressed endogenous gene locus promoter.

2. The method of claim 1, wherein the pluripotent cell is an embryonic stem cell, zygote or sperm cell.

3. The method of claim 1, wherein a splice acceptor sequence is operatively associated with the heterologous DNA.

4. The method of claim 1, wherein the heterologous DNA segment is a general deletor cassette comprising a gene encoding a recombinase.

5. The method of claim 4, wherein the heterologous DNA segment is a general deletor cassette further comprising an Internal Ribosome Entry Site upstream of the gene encoding a recombinase.

6. The method of claim 4, wherein a splice acceptor sequence is operatively associated with the gene encoding the recombinase.

7. The method of claim 4, wherein the recombinase is Cre or Flp.

8. The method of claim 4, wherein the general deletor cassette comprises a splice acceptor sequence operatively associated with a gene encoding Cre upstream of a positive selection cassette comprising a PGK promoter operatively associated with a gene encoding neo.

9. The method of claim 8, wherein the general deletor cassette further comprises a[008e] Internal Ribosome Entry Site upstream of the gene encoding Cre.

10. The method of claim 1, wherein the general deletor cassette further comprises downstream of the heterologous DNA a positive selection cassette.

11. The method of claim 10, wherein the positive selection cassette comprises a DNA sequence encoding a promoter operatively associated with a gene encoding a selectable marker.

12. The method of claim 11, wherein the selectable marker is neo.

13. The method of claim 1, wherein the heterologous DNA segment encodes a general reporter cassette comprising a DNA stuffer sequence flanked by two recombinase recognition sequences in the same orientation upstream of a DNA sequence encoding a reporter.

14. The method of claim 13, further comprising a splice acceptor operatively associated with the DNA stuffer sequence.

15. The method of claim 13, wherein the DNA stuffer sequence comprises a promoter operatively associated with a gene encoding a selectable marker and at least one polyadenylation sequence.

16. The method of claim 15 wherein the selectable marker is neo.

17. The method of claim 13, wherein the reporter is β-galactosidase.

18. The method of claim 15, wherein the promoter is PGK.

19. The method of claim 13, wherein the recombinase recognition sequences are lox or frt.

20. The method of claim 13, wherein the general reporter cassette comprises a spliceacceptor operatively associated with a DNA stuffer sequence comprising a PGK promoter operatively associated with a gene encoding neo and four polyadenylation sequences, the DNA stuffer sequence flanked by two lox sites in the same orientation and the DNA stuffer sequence is positioned upstream of a gene encoding β-galactosidase.

21. A general targeting construct comprising a targeting region inserted in at least 100 base pairs of a DNA sequence homologous with a ROSA26 or G3BP(BT5) endogenous gene, locus; wherein the targeting region comprises a heterologous gene, and optionally further comprises a DNA stuffer sequence, a deletor cassette, a positive selection cassette, a reporter cassette or a positively selectable marker, whereby the heterologous gene can be ubiquitously expressed when integrated at the endogenous gene locus.

22. The construct of claim 21, further comprising a negative selection cassette.

23. The construct of claim 21, wherein the endogenous gene locus is ROSA26.

24. The construct of claim 23, wherein the homologous DNA sequence comprises 5 kb of the ROSA26 endogenous gene locus.

25. The construct of claim 21, wherein the endogenous gene locus is G3BP (BT5).

26. A general deletor construct comprising a gene encoding a recombinase inserted in at least 100 base pairs of a DNA sequence homologous with a ROSA26 or G3BP(BT5) endogenous gene locus comprising a promoter;

whereby the gene encoding the recombinase is inserted in a 5' to 3' direction relative to the transcription direction of the endogenous gene locus promoter when the construct is integrated at the endogenous gene locus, such that the recombinase is expressed by the endogenous gene locus promoter.

27. The construct of claim 25, further comprising a negative selection cassette.

28. The construct of claim 27, wherein the negative selection cassette comprises a PGK promoter operatively associated with a gene encoding Diphtheria toxin.

29. The construct of claim 25, wherein a splice acceptor sequence is operatively associated with a 5' end of the gene encoding the recombinase.

30. The construct of claim 25, further comprising a positive selection cassette within the homologous DNA sequence.

31. The construct of claim 30, wherein the positive selection cassette comprises a promoter operatively associated with a positively selectable marker.

32. The construct of claim 31, wherein the positively selectable marker is neo.

33. The construct of claim 25, wherein the endogenous gene locus is ROSA26.

34. The construct of claim 26, wherein the endogenous gene locus is G3BP(BT5).

35. The construct of claim 26, further comprising an Internal Ribosome Entry Site operatively associated with a 5' end of the gene encoding the recombinase.

36. A general reporter construct comprising at least 100 base pairs of a DNA sequence homologous with a ROSA26 or G3BP(BT5) endogenous gene locus, and, in a 5' to 3' direction relative to the transcription direction when the construct is integrated at the ROSA26 or G3BP(BT5) gene locus.

a DNA stuffer sequence flanked by recombinase recognition sequences and a gene encoding a reporter;

whereby the gene encoding the reporter is expressed when the construct is integrated at the ROSA26 or G3BP (BT5) endogenous gene locus and the DNA stuffer sequence is removed.

37. The construct of claim 36, further comprising a negative selection cassette.

38. The construct of claim 37, wherein the negative selection cassette comprises a PGK promoter operatively associated with a gene encoding Diphtheria toxin.

39. The construct of claim 36, further comprising a splice acceptor sequence operatively associated with the DNA stuffer sequence, wherein the DNA stuffer sequence and flanking recombination recognition sequences are positioned between the splice acceptor sequence and the gene encoding the reporter.

40. The construct of claim 36, wherein the DNA stuffer sequence comprises a promoter operatively associated with a gene encoding a selectable marker and at least one polyadenylation sequence.

41. The construct of claim 40, wherein the selectable marker is neo.

42. The construct of claim 40, wherein the promoter is PGK.

43. The construct of claim 36, wherein the reporter is β-galactosidase.

44. The construct of wherein claim 36, the DNA stuffer sequence comprises a PGK promoter operatively associated with a gene encoding neo and four polyadenylation sequences, and wherein the DNA stuffer sequence is flanked by two lox sites in the same orientation.

45. The construct of claim 36, wherein the endogenous gene locus is ROSA26.

46. The construct of claim 36, wherein the endogenous gene locus is G3BP(BT5).

47. The construct of claim 36, further comprising a positive selection cassette within the homologous DNA sequence.

48. The construct of claim 36, wherein the recombinase recognition sequences are lox or frt sites.

* * * * *

UNITED STATES PATENT AND TRADEMARK OFFICE
CERTIFICATE OF CORRECTION

PATENT NO.    : 6,461,864 B1
DATED         : October 8, 2002
INVENTOR(S)   : Philippe Soriano and Elizabeth J. Robertson It is certified that error appears in the above-identified patent and that said Letters Patent is hereby corrected as shown below:

<u>Title page,</u>
Item [73], Assignee, after "Fred Hutchinson Cancer Research Center, Seattle, WA (US)" please insert -- President and Fellows of Harvard University, Cambridge, MA (US) --.

Signed and Sealed this

Tenth Day of June, 2003

JAMES E. ROGAN
*Director of the United States Patent and Trademark Office*